United States Patent
D'Antona et al.

(10) Patent No.: US 8,381,752 B2
(45) Date of Patent: Feb. 26, 2013

(54) PROCESS FOR REDUCING THE RESTART PRESSURE OF STREAMS SELECTED FROM WAXY CRUDE OILS, WATER-IN-CRUDE EMULSIONS AND DISPERSIONS OF HYDROCARBON HYDRATES

(75) Inventors: Paolo D'Antona, Assago-Milano (IT); Thomas Paul Lockhart, Lodi (IT); Alberto Di Lullo, Peschiera Borromeo-Milano (IT)

(73) Assignee: ENI S.p.A., Rome (IT)

( * ) Notice: Subject to any disclaimer, the term of this patent is extended or adjusted under 35 U.S.C. 154(b) by 190 days.

(21) Appl. No.: 12/977,511

(22) Filed: Dec. 23, 2010

(65) Prior Publication Data

US 2011/0162722 A1    Jul. 7, 2011

Related U.S. Application Data

(62) Division of application No. 11/572,295, filed as application No. PCT/EP2005/007819 on Jul. 18, 2005, now Pat. No. 7,896,020.

(30) Foreign Application Priority Data

Jul. 22, 2004    (IT) .............................. MI2004A1480

(51) Int. Cl.
    *F17D 1/16*    (2006.01)
(52) U.S. Cl. ................................. 137/13; 137/7; 137/92
(58) Field of Classification Search ..................... 137/13, 137/4, 92, 3, 7; 73/54.01
    See application file for complete search history.

(56) References Cited

U.S. PATENT DOCUMENTS

| | | | |
|---|---|---|---|
| 3,575,469 A | 4/1971 | Meyer | |
| 3,780,750 A | 12/1973 | Perkins | |
| 3,910,299 A * | 10/1975 | Tackett et al. | 406/197 |
| 4,137,025 A | 1/1979 | Graves et al. | |
| 4,551,041 A | 11/1985 | Coon et al. | |
| 4,697,426 A * | 10/1987 | Knowles, Jr. | 62/46.1 |
| 4,974,617 A | 12/1990 | Simon | |
| 4,982,756 A | 1/1991 | Scribner | |
| 5,717,181 A | 2/1998 | Colgate | |
| 6,656,366 B1 * | 12/2003 | Fung et al. | 210/737 |
| 7,219,734 B2 | 5/2007 | Bai et al. | |
| 7,357,030 B2 | 4/2008 | Novascone et al. | |
| 2002/0187085 A1 * | 12/2002 | Fung et al. | 422/189 |

FOREIGN PATENT DOCUMENTS

| | | |
|---|---|---|
| WO | 99/57482 | 11/1999 |
| WO | 02/25062 | 3/2002 |
| WO | 03/012401 | 2/2003 |

* cited by examiner

*Primary Examiner* — Kevin Lee
(74) *Attorney, Agent, or Firm* — Oblon, Spivak, McClelland, Maier & Neustadt, L.L.P.

(57) ABSTRACT

For reducing the restart pressure of streams selected from waxy crude oils, water-in-crude emulsions and dispersions of hydrocarbon hydrates, at least partially structured, a mechanic disturbance is applied, in flow-stop conditions, on the streams. The temperatures are lower than the WAT (Wax Appearance Temperature) for the waxy crude oils and water-in-crude emulsions. The temperatures are also lower than the forming temperatures of the hydrates and pressures higher than the forming pressure of the hydrates, for the dispersions of hydrocarbon hydrates.

7 Claims, 27 Drawing Sheets

Schematic representation of the structuring process, with time, of a stream under flow-stop conditions

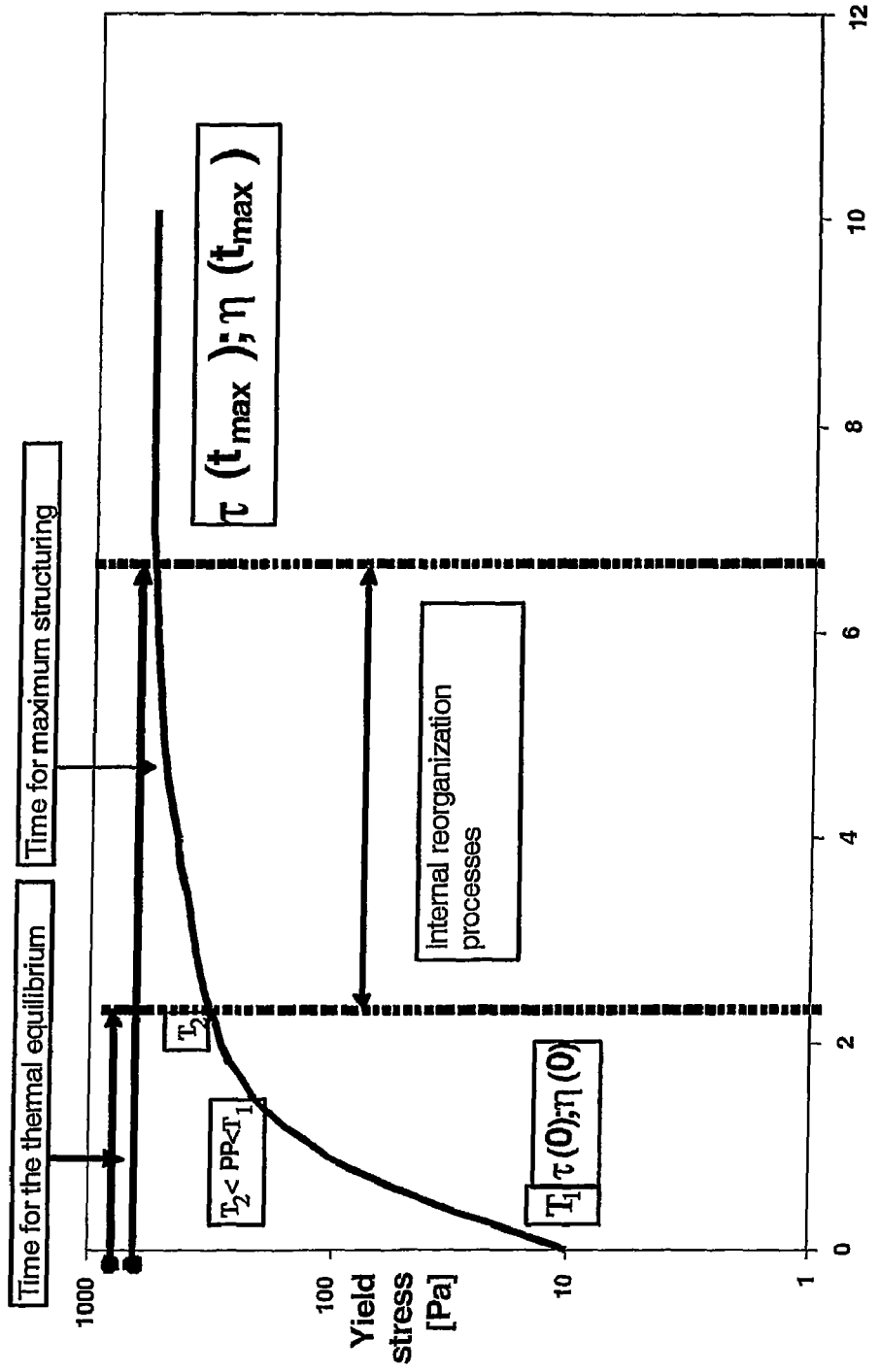
Fig.1 – Schematic representation of the structuring process, with time, of a stream under flow-stop conditions

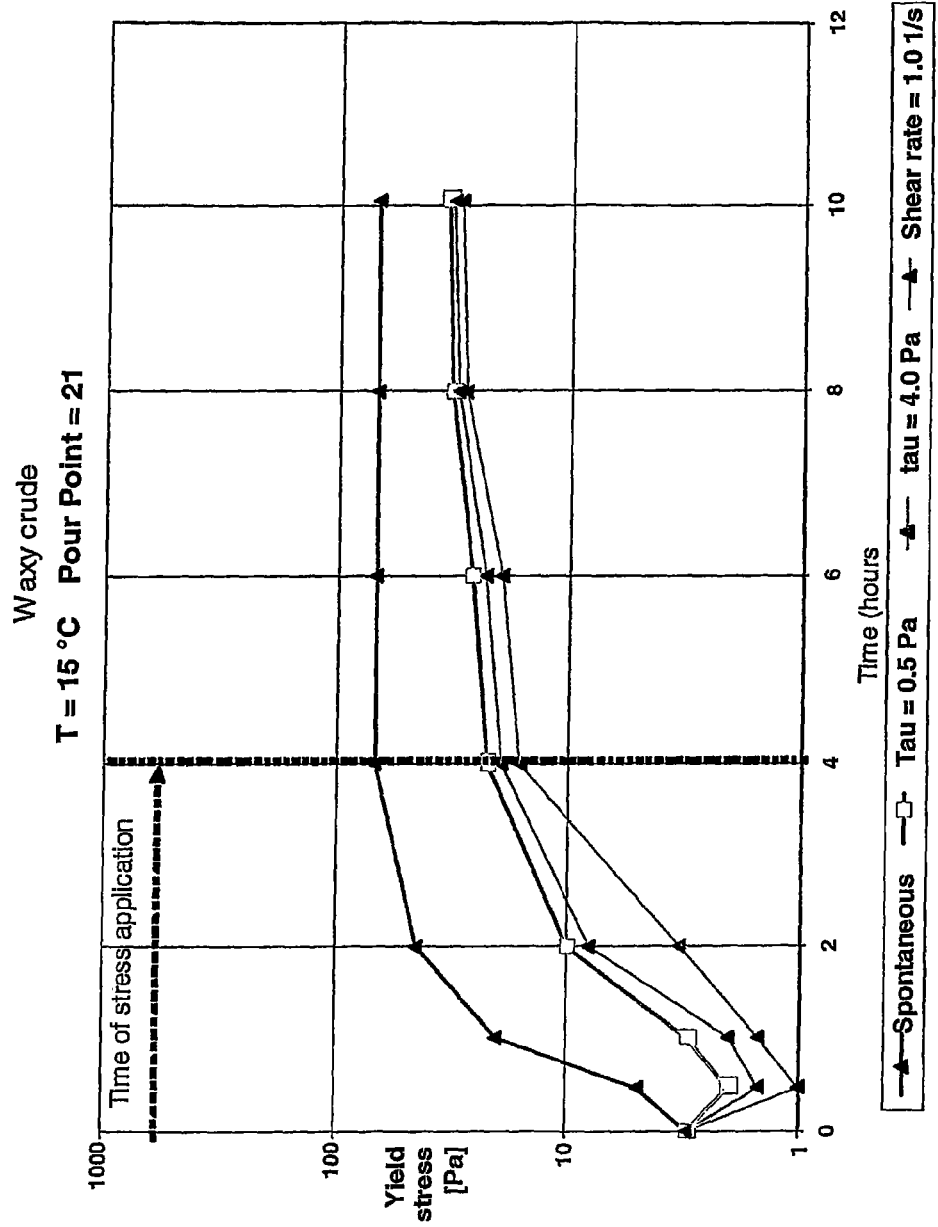
Fig.2 – Influence of the application of de-structuring mechanical stress on a stream consisting of a waxy crude in the absence of flow and temperature lower than the Pour Point

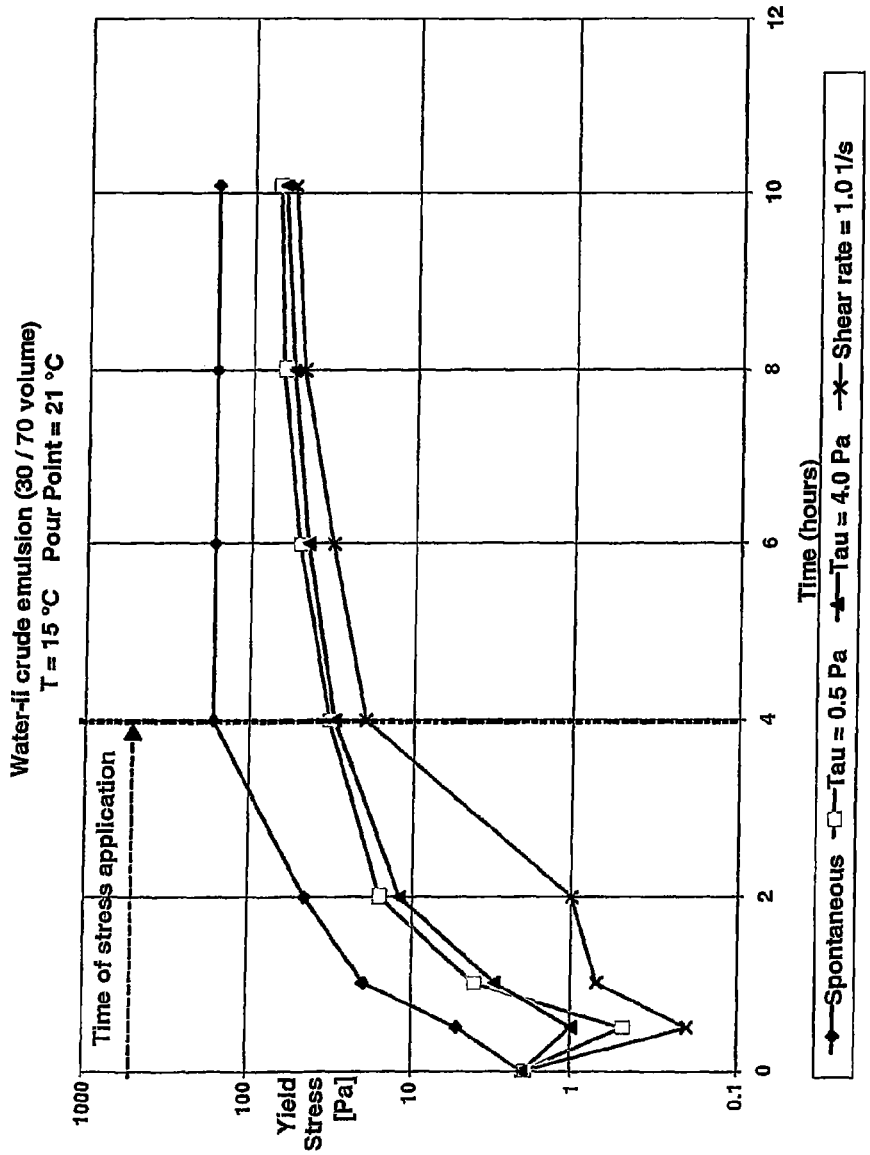
Fig.3 – Influence of the application of de-structuring mechanical stress on a stream consisting of a water-in-waxy crude emulsion in the absence of flow and temperature lower than the Pour Point

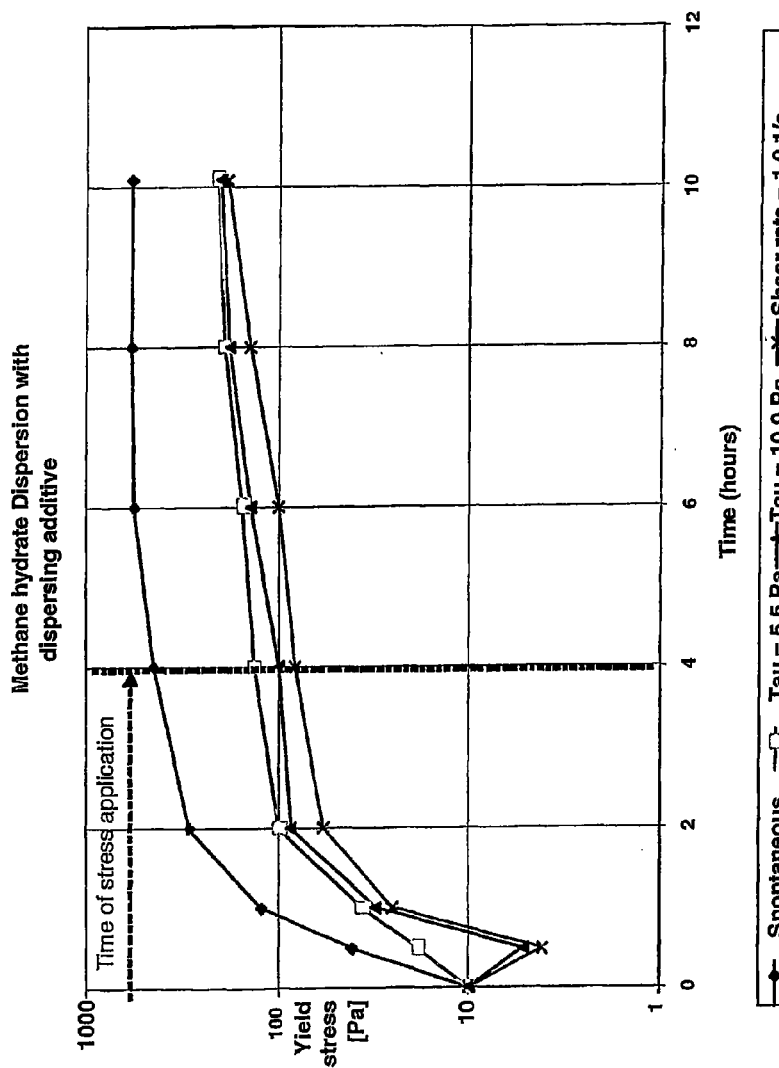
Fig. 4 – Influence of the application of de-structuring mechanical stress on a stream consisting of methane hydrate dispersion in crude oil, in the absence of flow and at the temperature and pressure of thermodynamic stability of hydrates

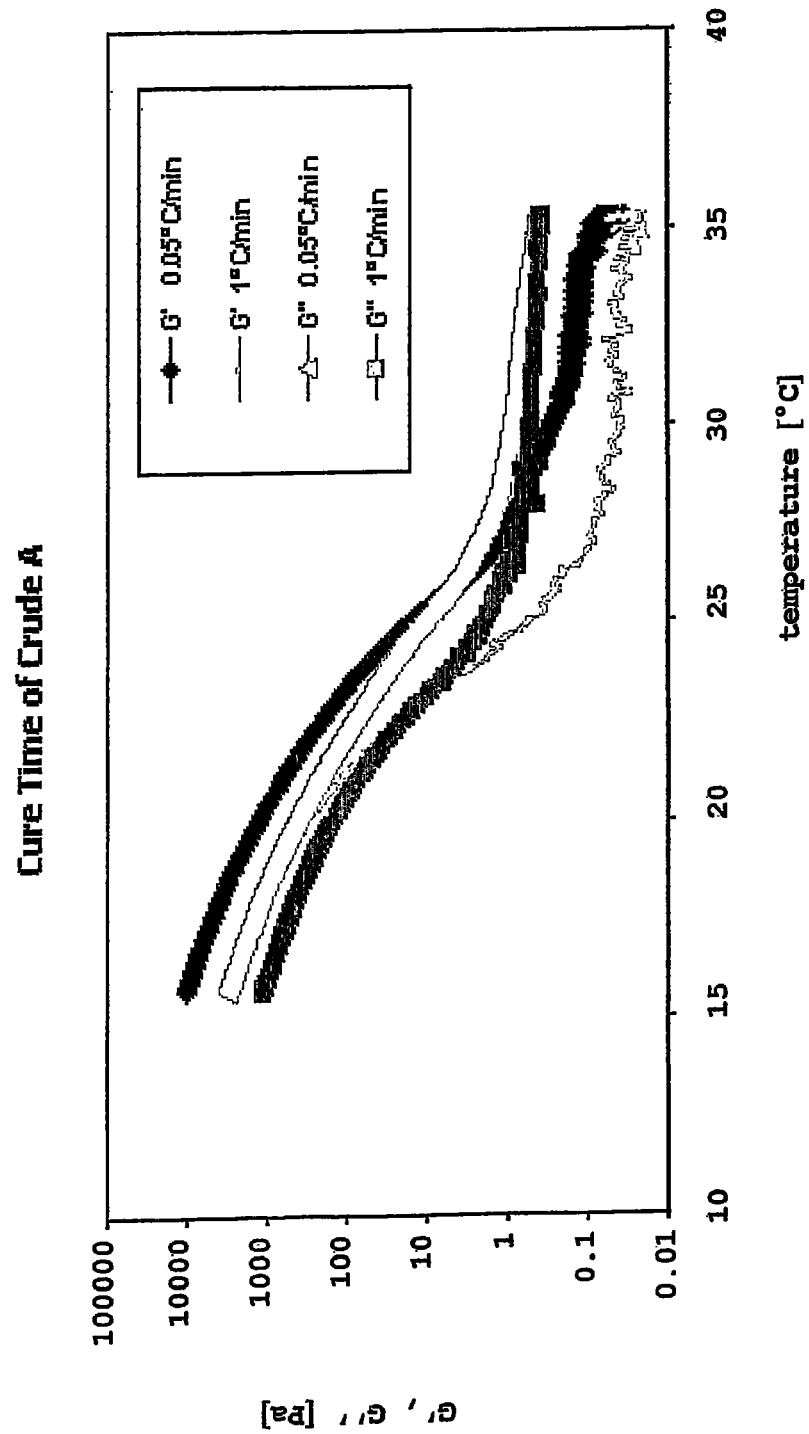
Fig. 5 – Variations of G' (tensile modulus) and G" (dissipative modulus) of a waxy crude with a variation in the temperature obtained by applying different cooling profiles

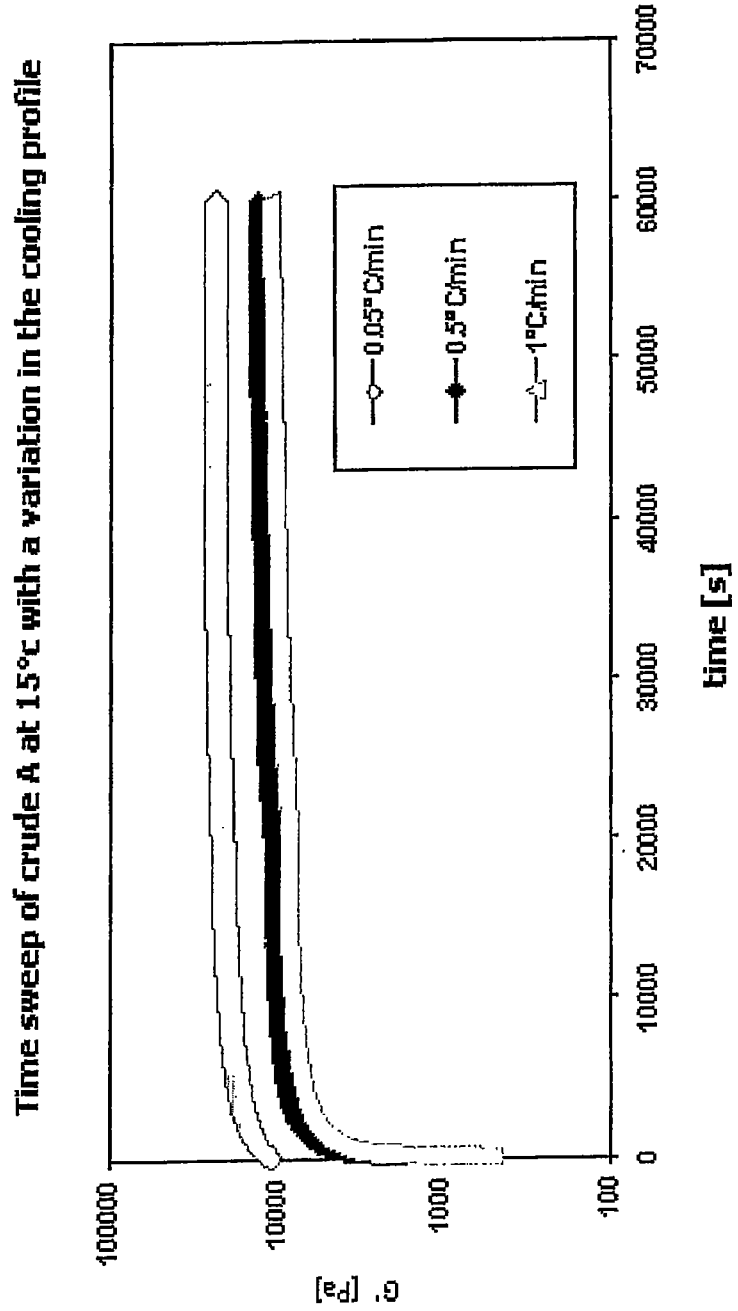
Fig. 6 – G' variation in relation to time (at a constant frequency of 1Hz and at a low deformation amplitude) at a temperature lower than the Pour Point for a waxy crude cooled with different termal profiles

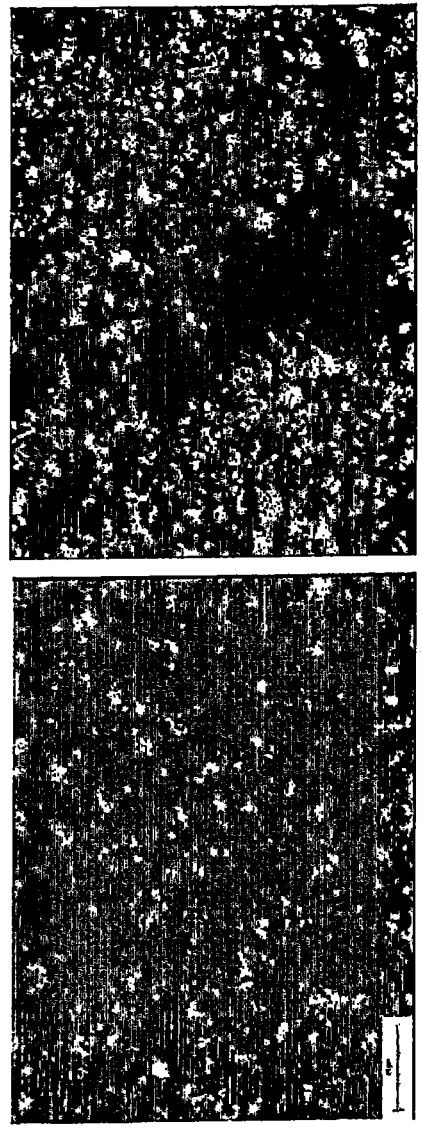
Fig.7 – Photos obtained by means of optical microscopy under polarized light of paraffin crystals of a crude cooled through two different thermal profiles (2°C/min and 0.05°C/min, respectively) and subsequent structuring time equal to 4 hrs.

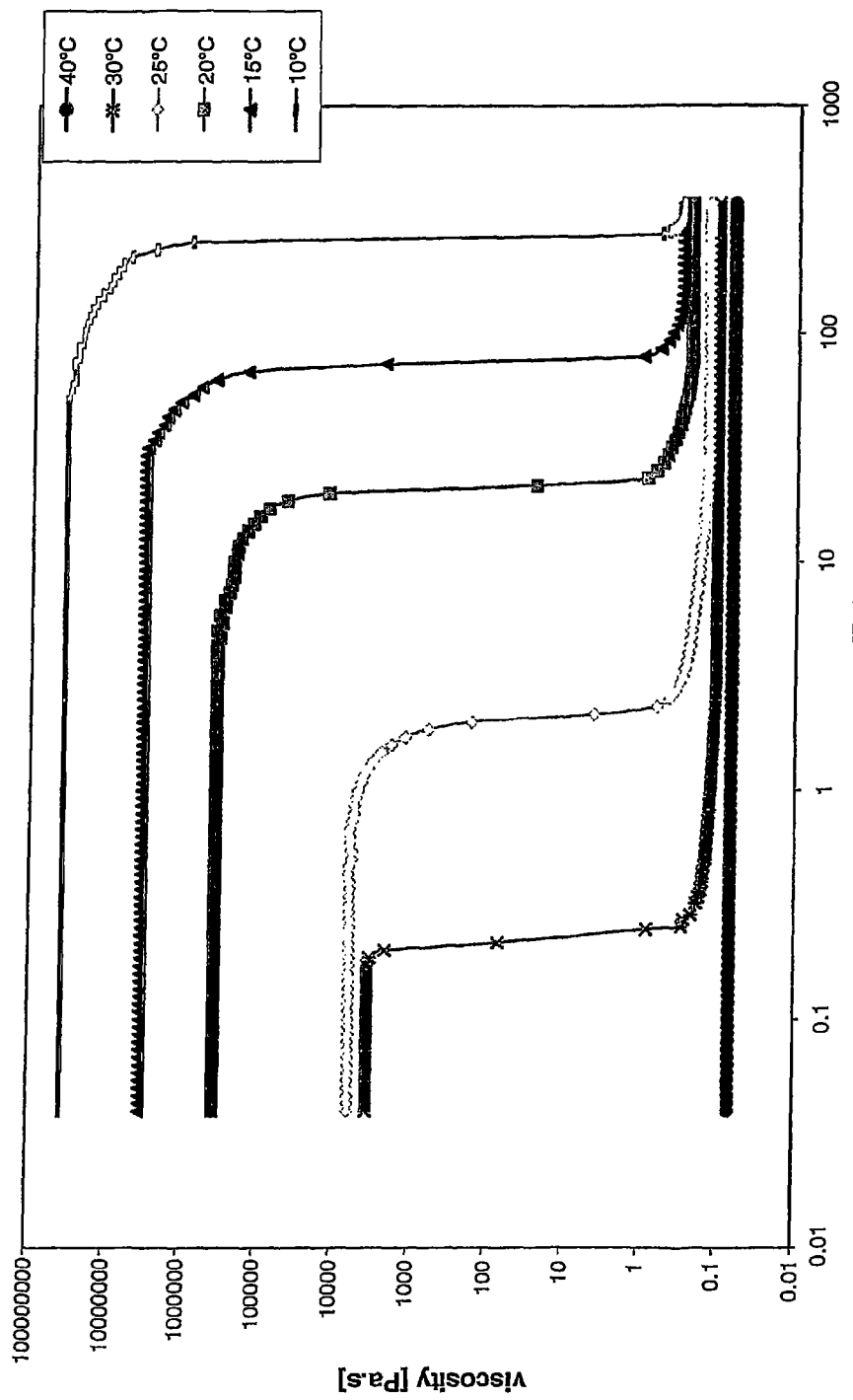
Fig. 8 – Waxy crude transition from a Newtonian to a non-Newtonian behaviour of the pseudo-plastic type, also for temperatures higher than the Pour Point (21°C)

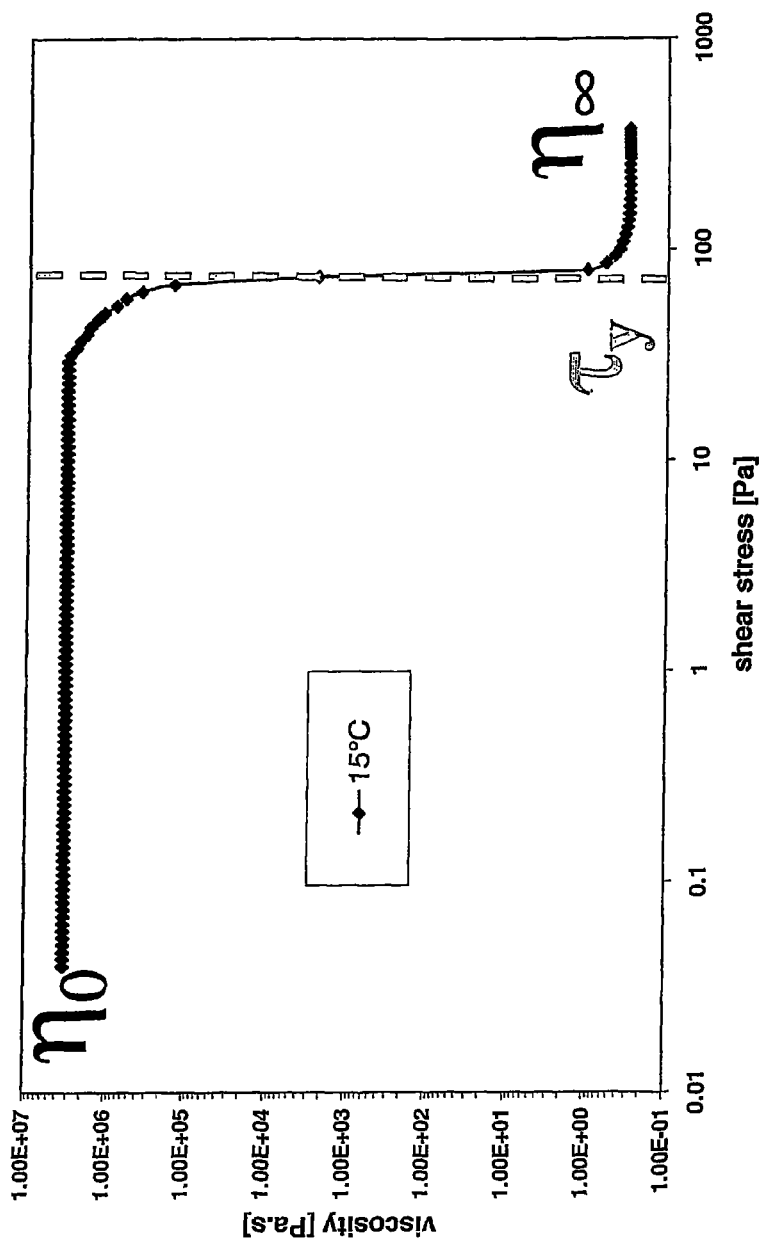
Fig. 9 – Viscosity vs stress profile of a waxy crude indicating the parameters which characterise the gel state, i.e. $\tau_y$, $\eta_0$ and $\eta_\infty$

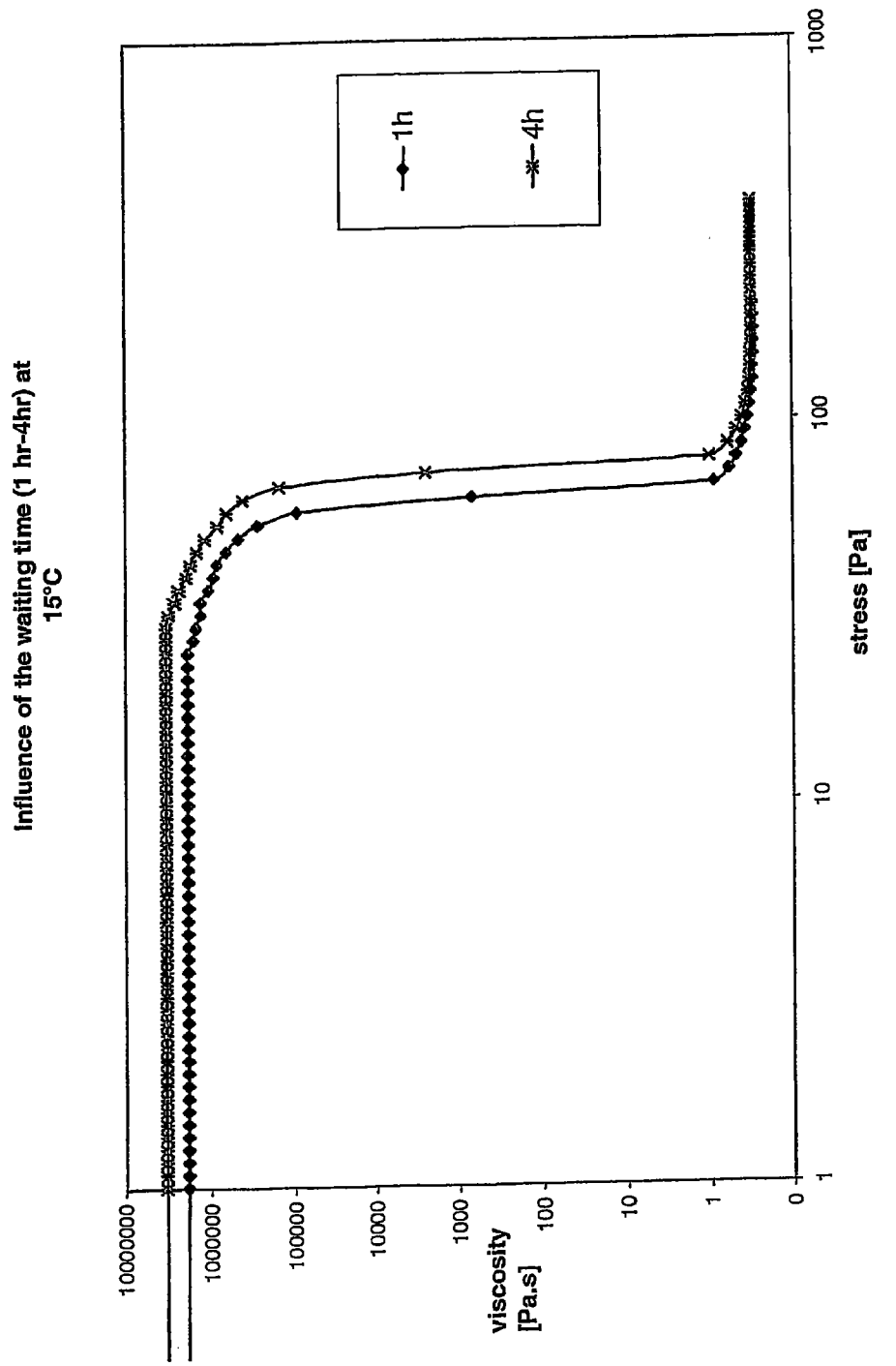
Fig. 10 – Flow curves of a structured waxy crude (temperature lower than the Pour Point) obtained by imposing a waiting time of 1 hour

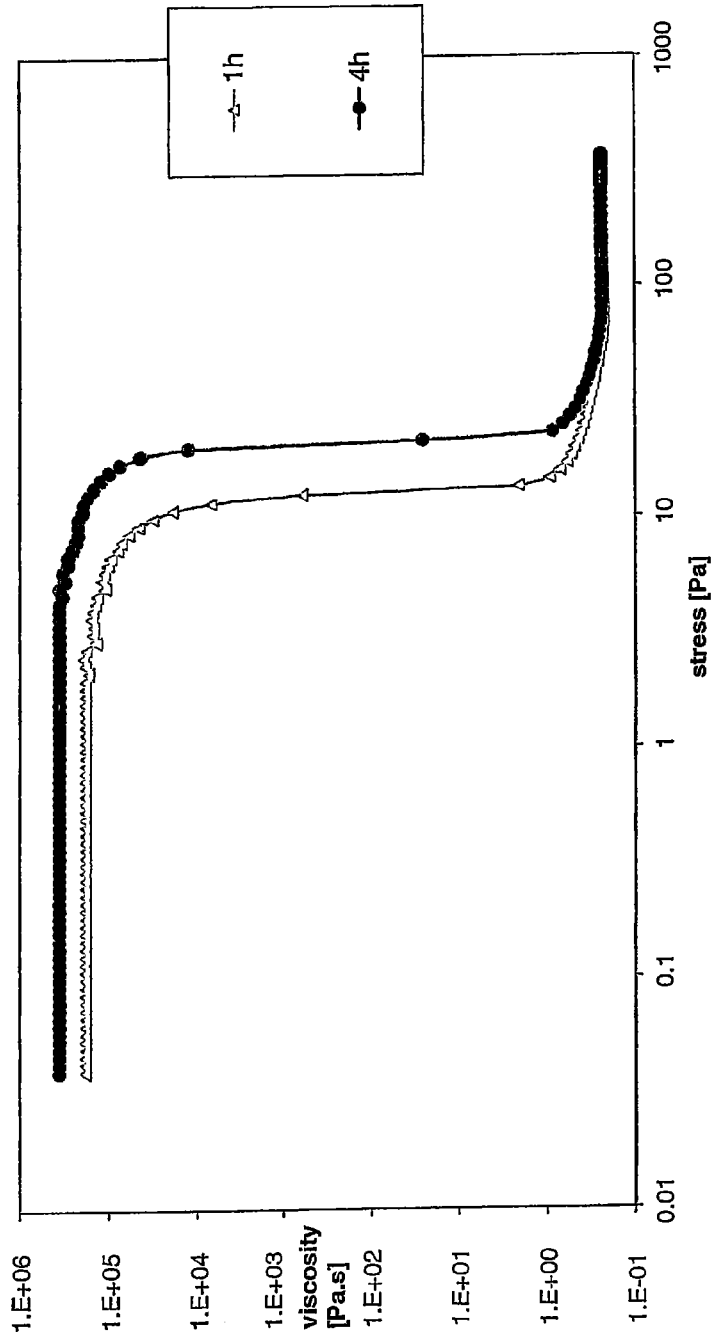
Fig.11 – Flow curves of a structured waxy crude (temperature lower than the Pour Point) obtained by imposing a waiting time of 4 hours.

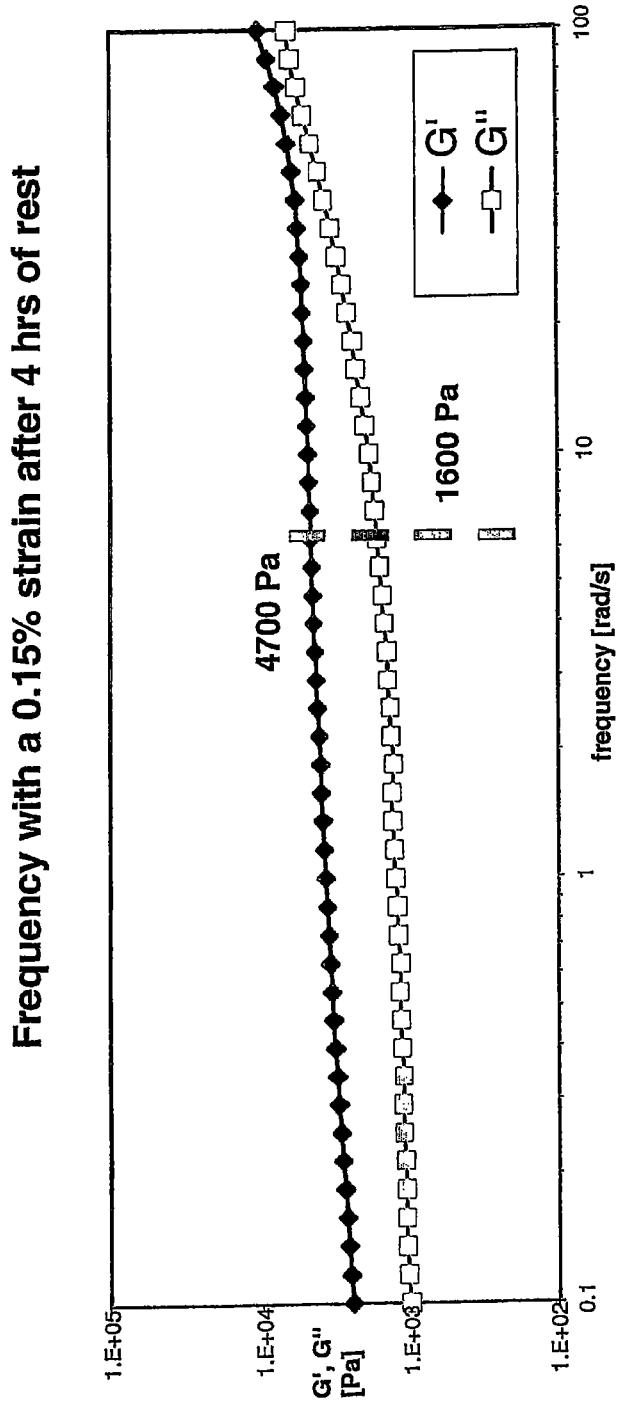
Fig.12 – Measurement under an oscillatory regime, at a low deformation amplitude, of module G' and module G" with a variation in frequency for a waxy crude stabilised at a temperature lower than the Pour Point, for four hours

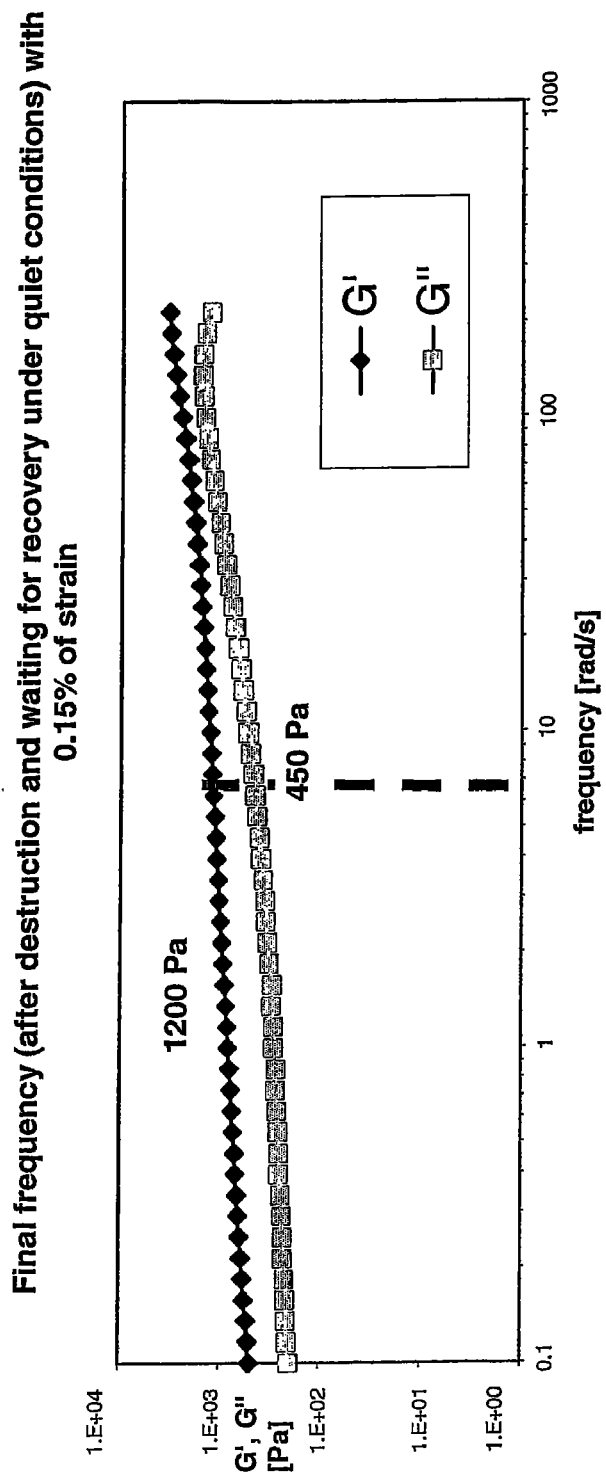
Fig.13 – Measurement under an oscillatory regime, at a low deformation amplitude, of module G' and module G" with a variation in frequency for a waxy crude at a temperature lower than the Pour Point, first subjected to triangular sequences of shear rates and then stabilized for four hours

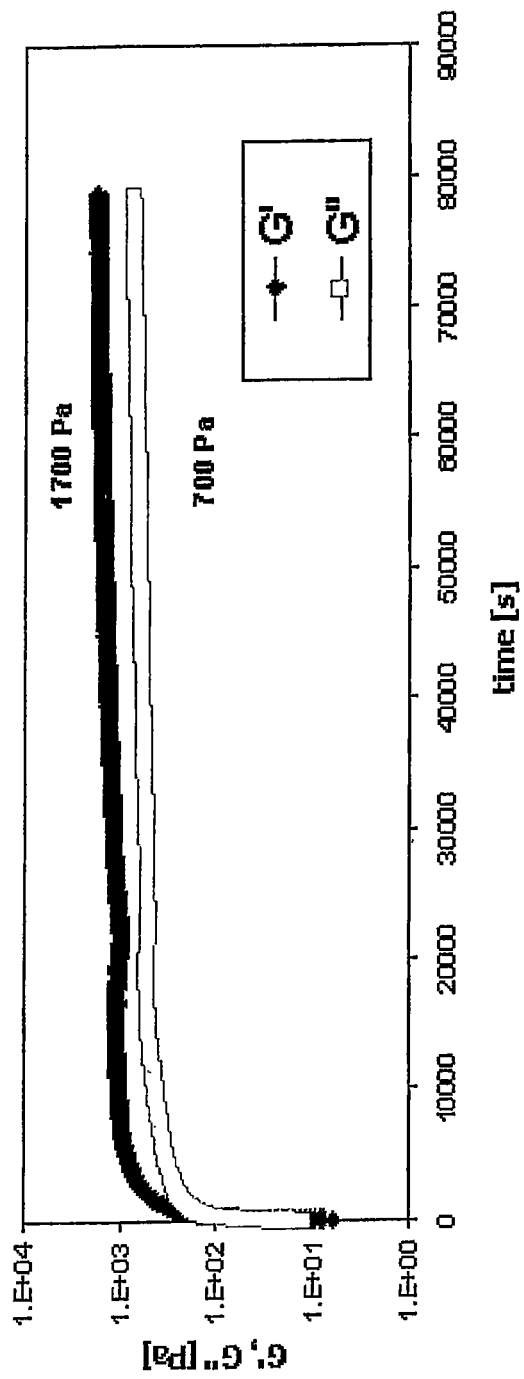
Fig. 14 – Measurement under an oscillatory regime, at a low deformation amplitude, of module G' and module G" with a variation in frequency for a waxy crude cooled to a temperature lower than the Pour Point, subjecting it to a constant shear rate equal to 1 s$^{-1}$ and then stabilised for four hours

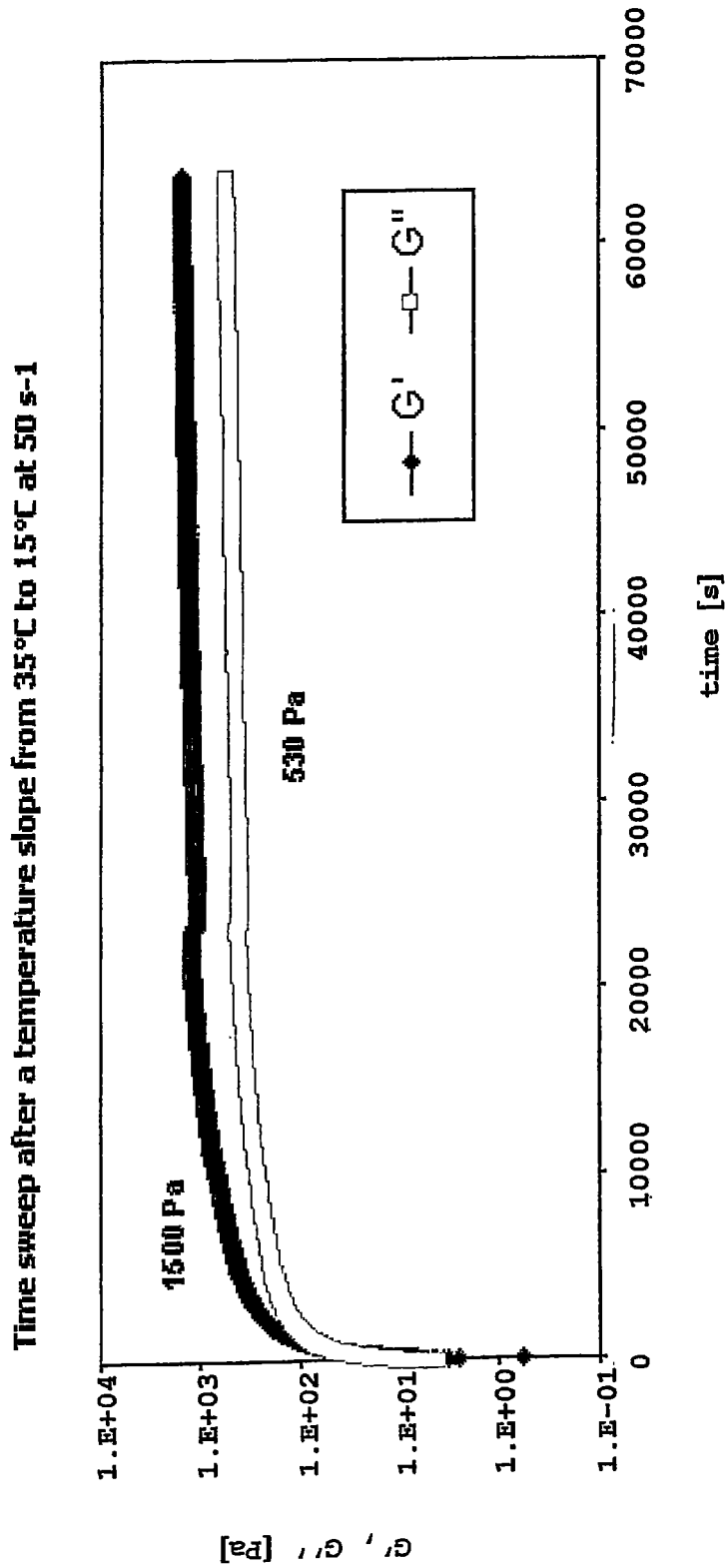
Fig.15 – Measurement under an oscillatory regime, at a low deformation amplitude, of module G' and module G" with a variation in frequency for a waxy crude cooled to a temperature lower than the Pour Point, subjecting it to a constant shear rate equal to 50 s$^{-1}$ and then stabilised for four hours

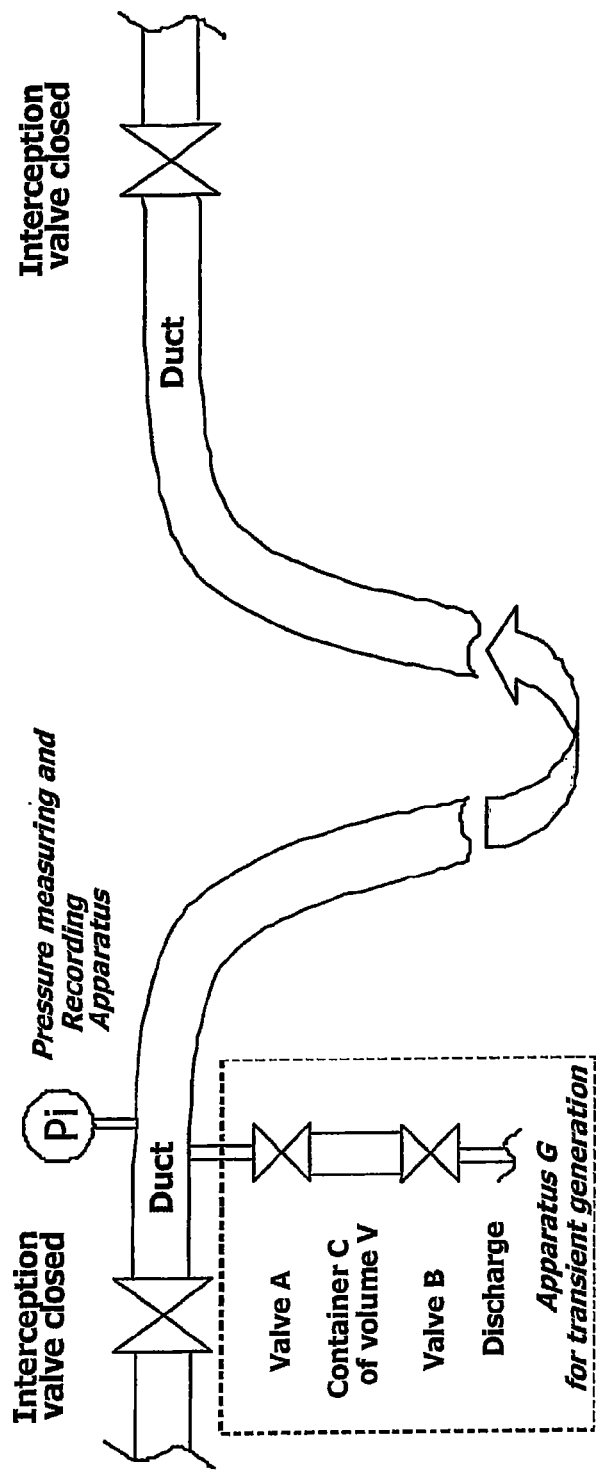
Fig.16 – Example of equipment for generating the stress object of the present invention

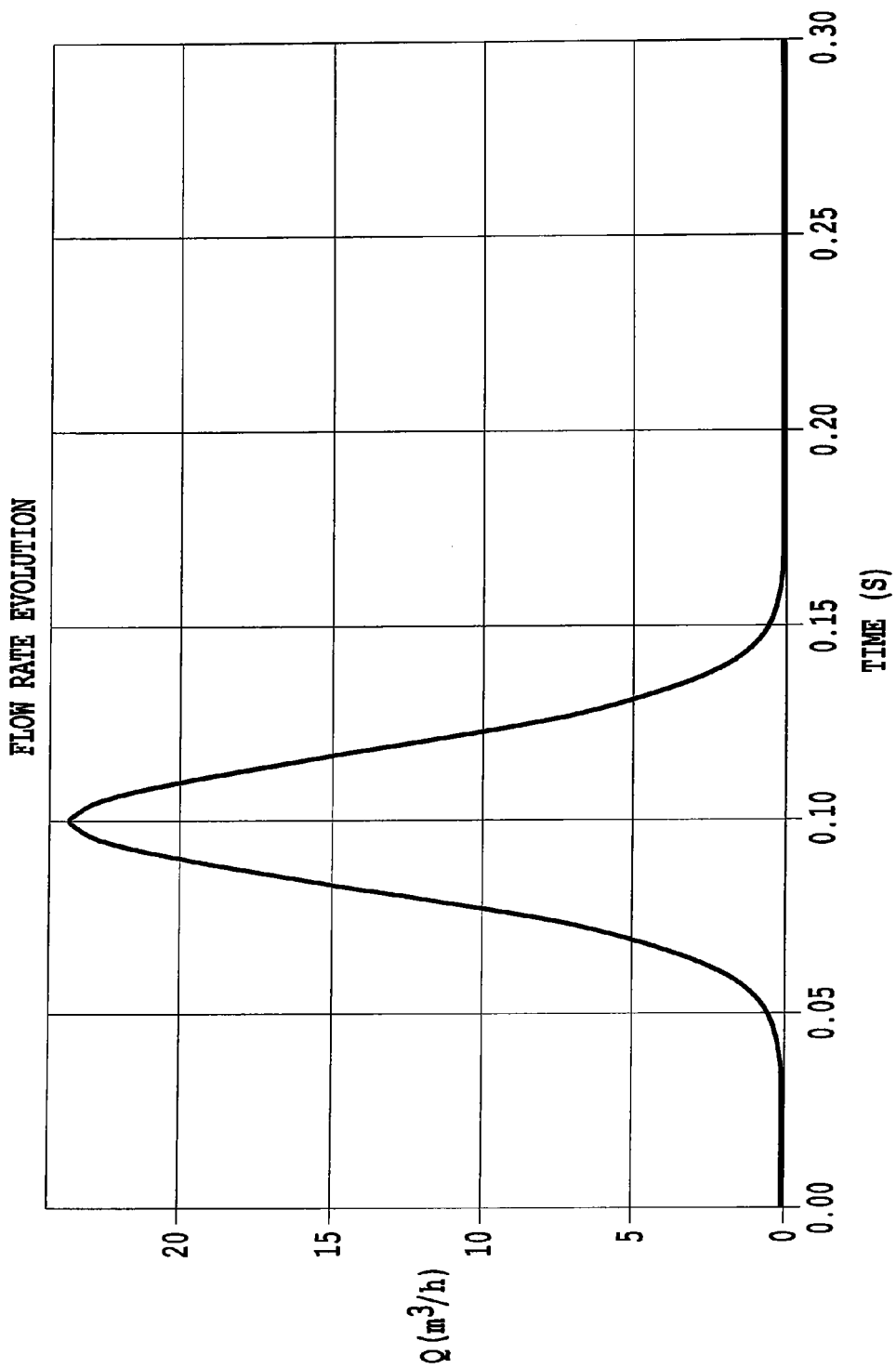
*Fig. 17* Example of the trend of the instant flow rate produced using the apparatus of Fig. 16.

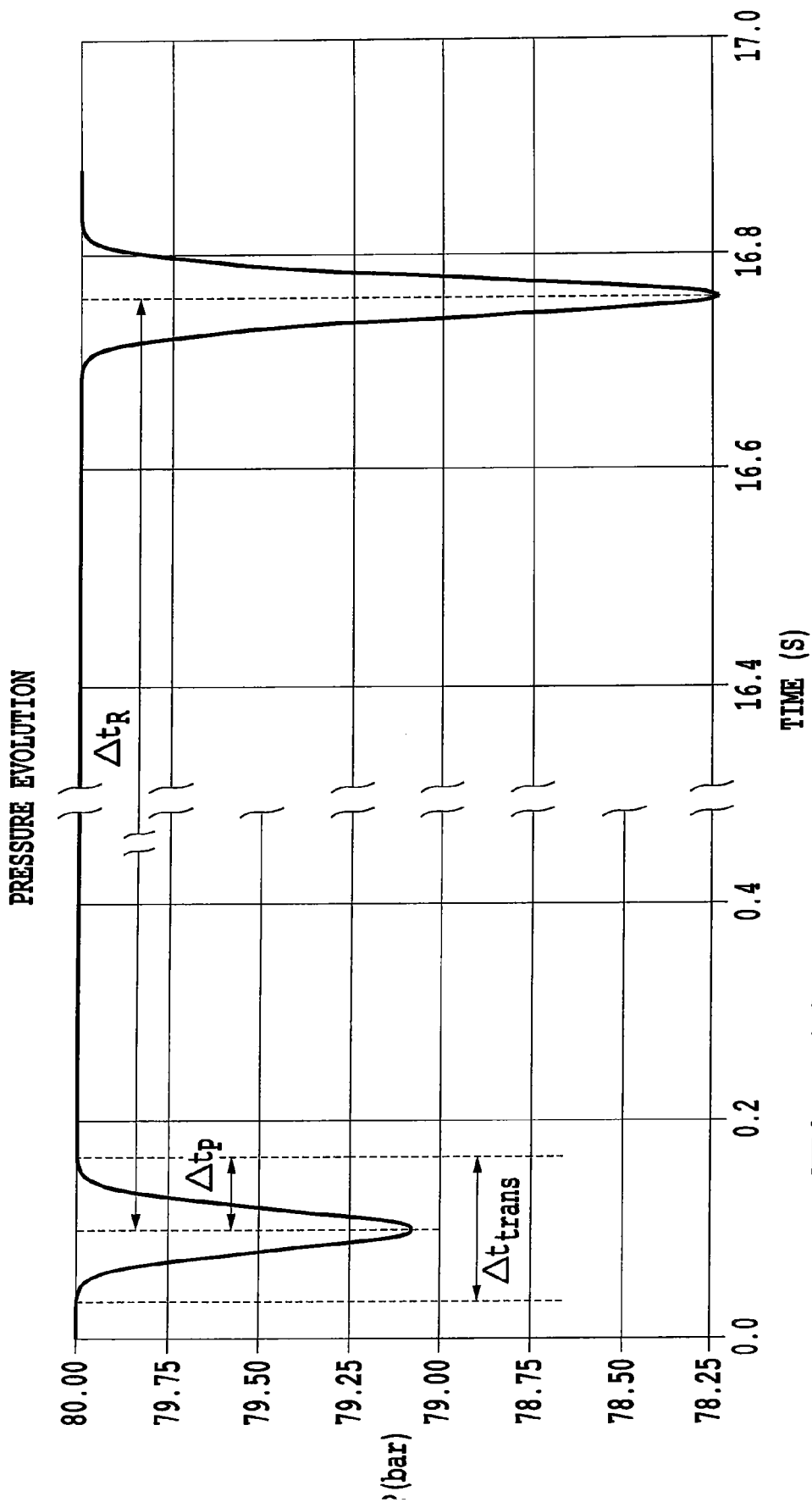
Fig. 18  Wave rebound time on the other end of the duct

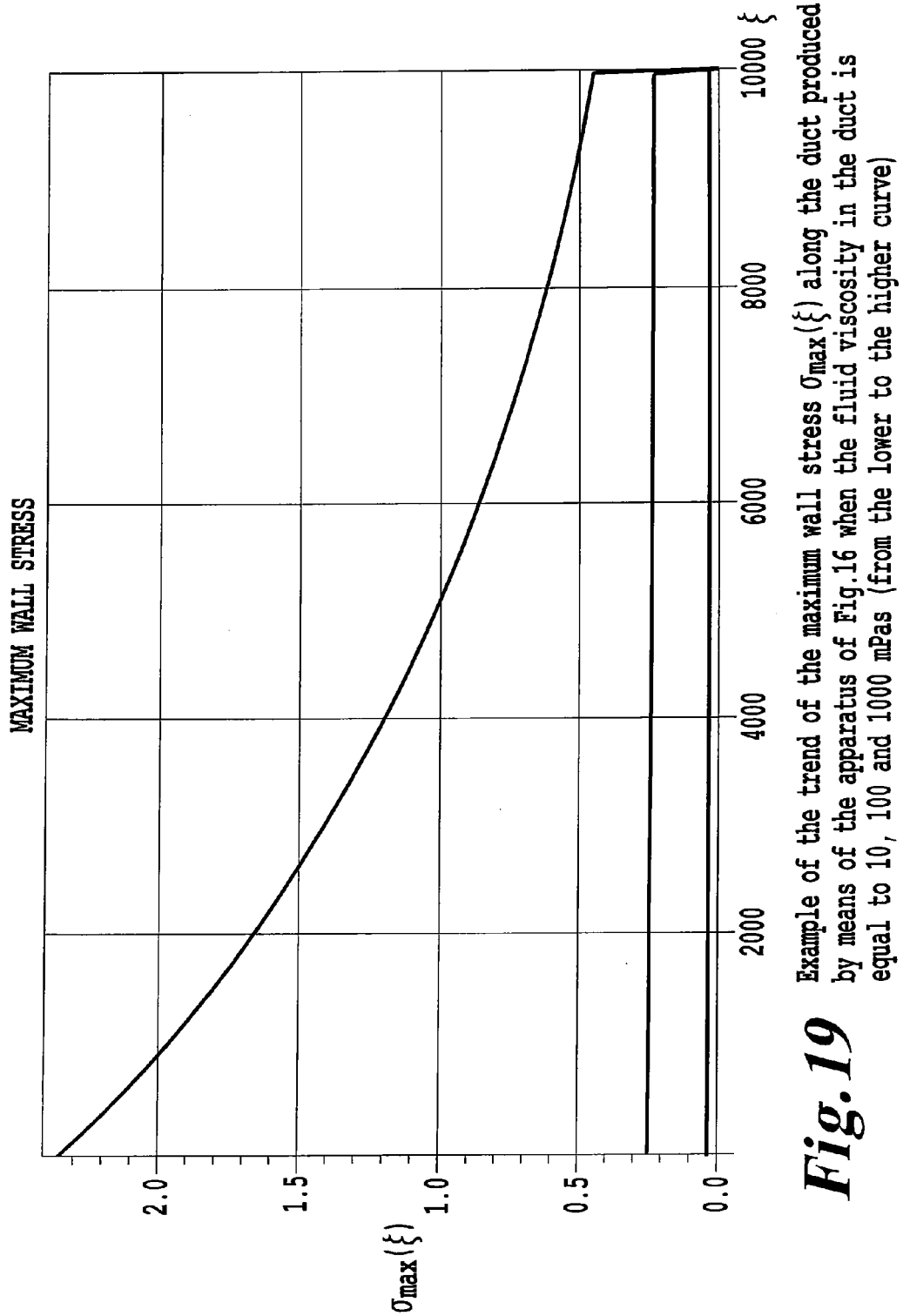
Fig. 19 Example of the trend of the maximum wall stress $\sigma_{max}(\xi)$ along the duct produced by means of the apparatus of Fig.16 when the fluid viscosity in the duct is equal to 10, 100 and 1000 mPas (from the lower to the higher curve)

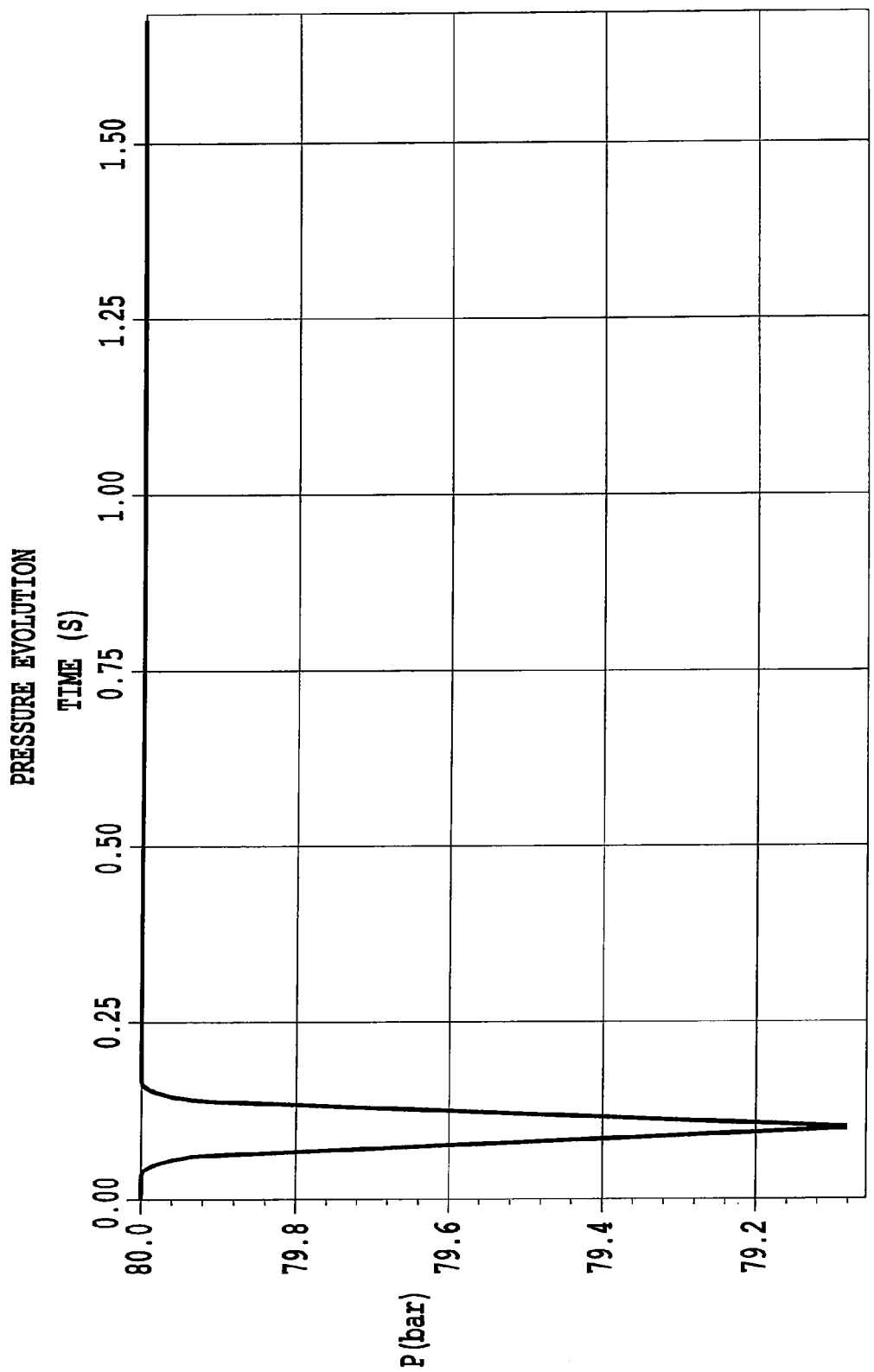
Fig. 20 Example of instant pressure evolution produced by the flow rate transient of Fig. 17

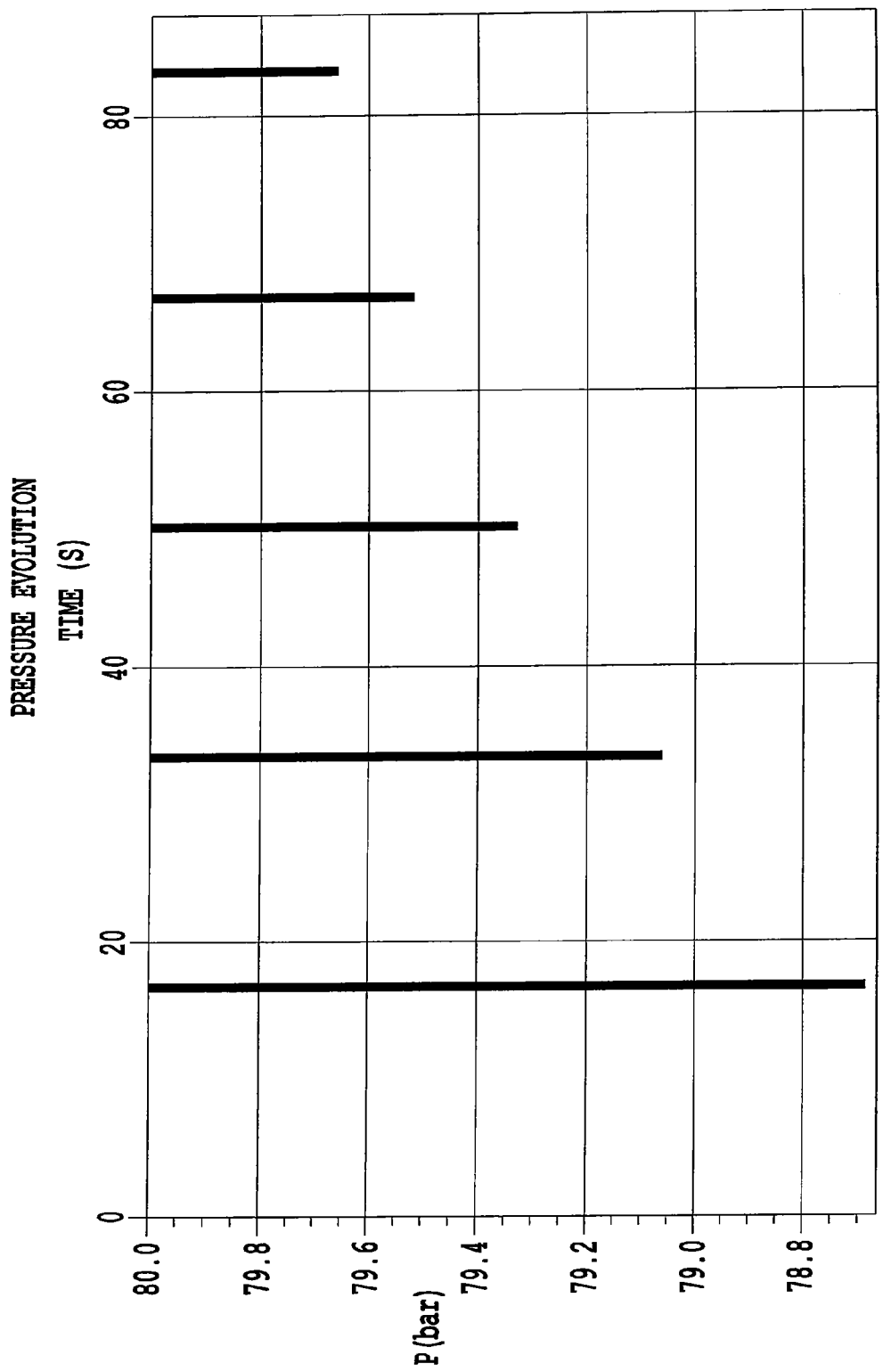
Fig. 21  Example of subsequent rebounds of the pressure peak of Fig. 20 on the duct extremis. The fluid viscosity in the duct is equal to 100 mPas

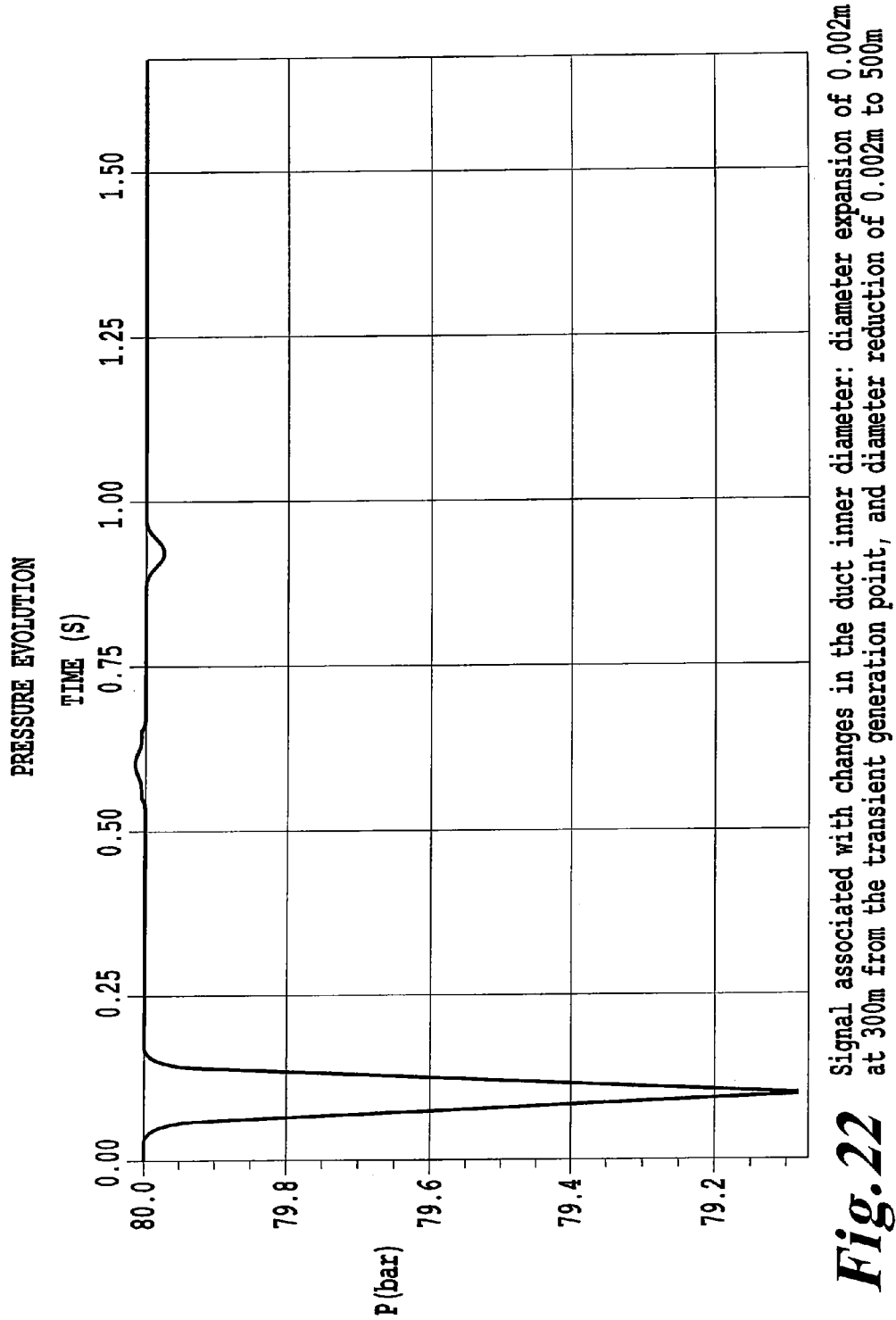
Fig. 22 Signal associated with changes in the duct inner diameter: diameter expansion of 0.002m at 300m from the transient generation point, and diameter reduction of 0.002m to 500m

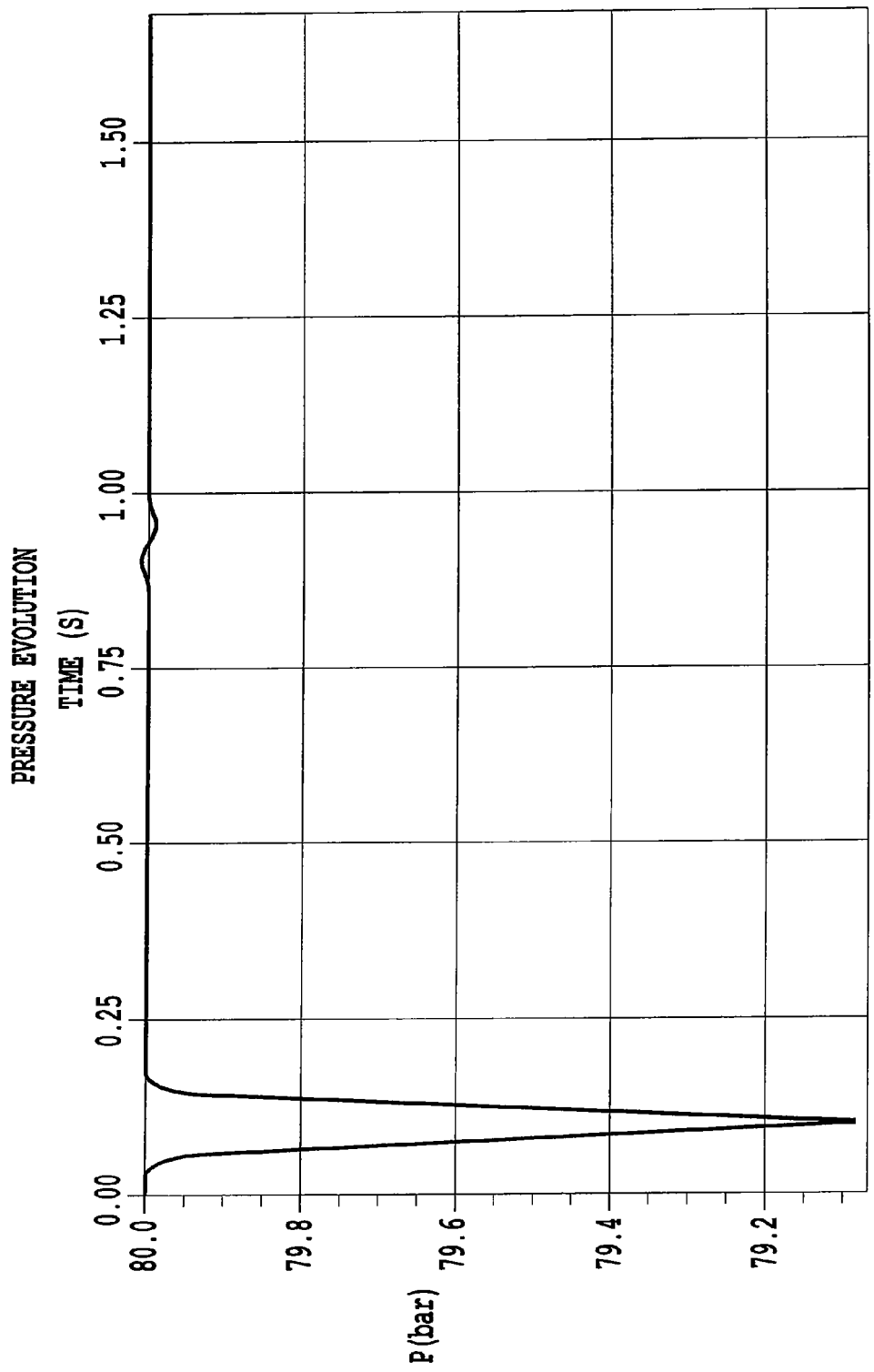
*Fig. 23* Signal associated with a localized restriction of the inner diameter of the duct: diameter restriction of 0.002m, 1m long, situated at 500m from the transient generation point

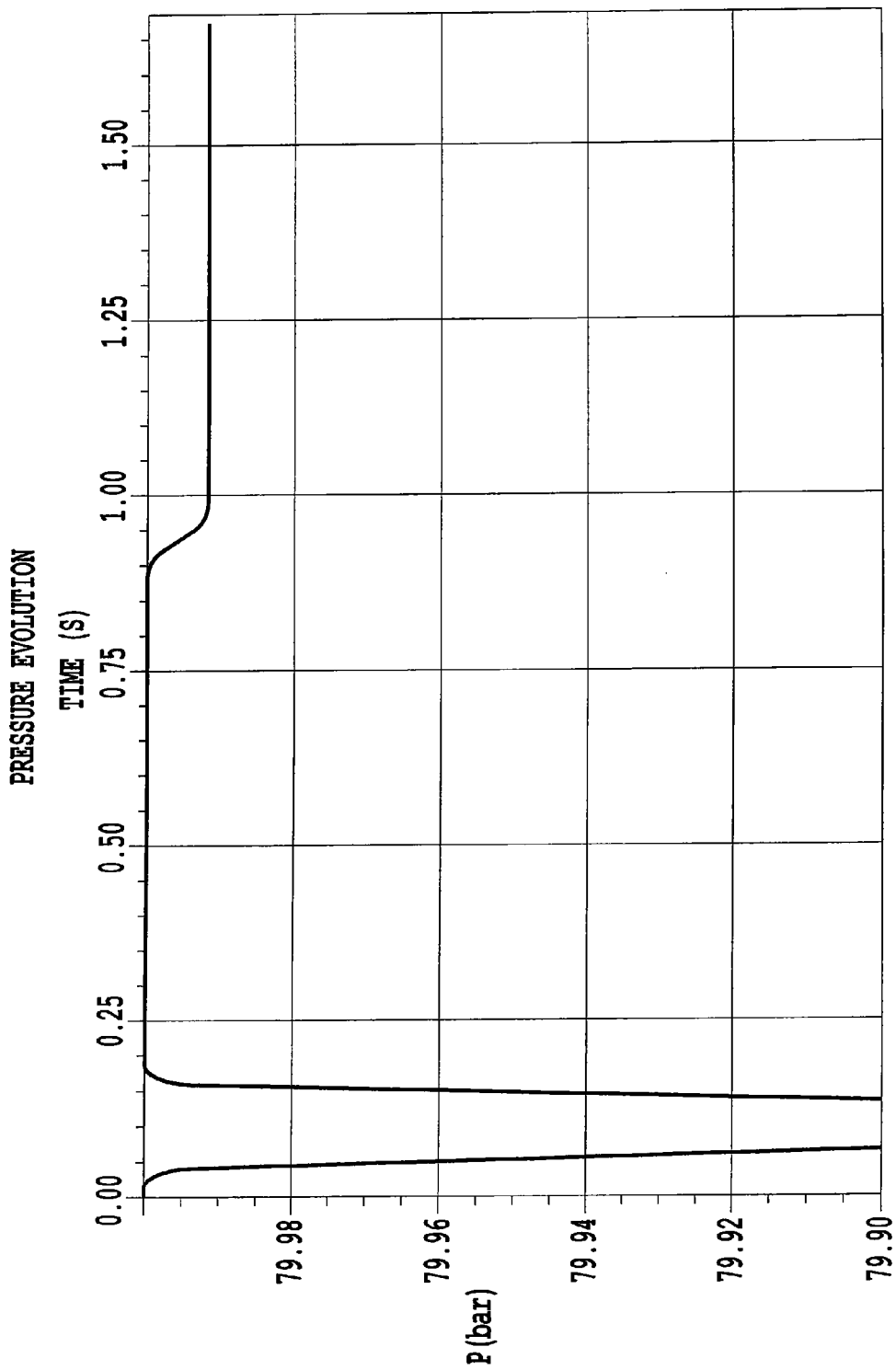
Fig. 24  Signal associated with a viscosità variation starting from 500m from the transient generation point: from 10 mPas to 1000 mPas.

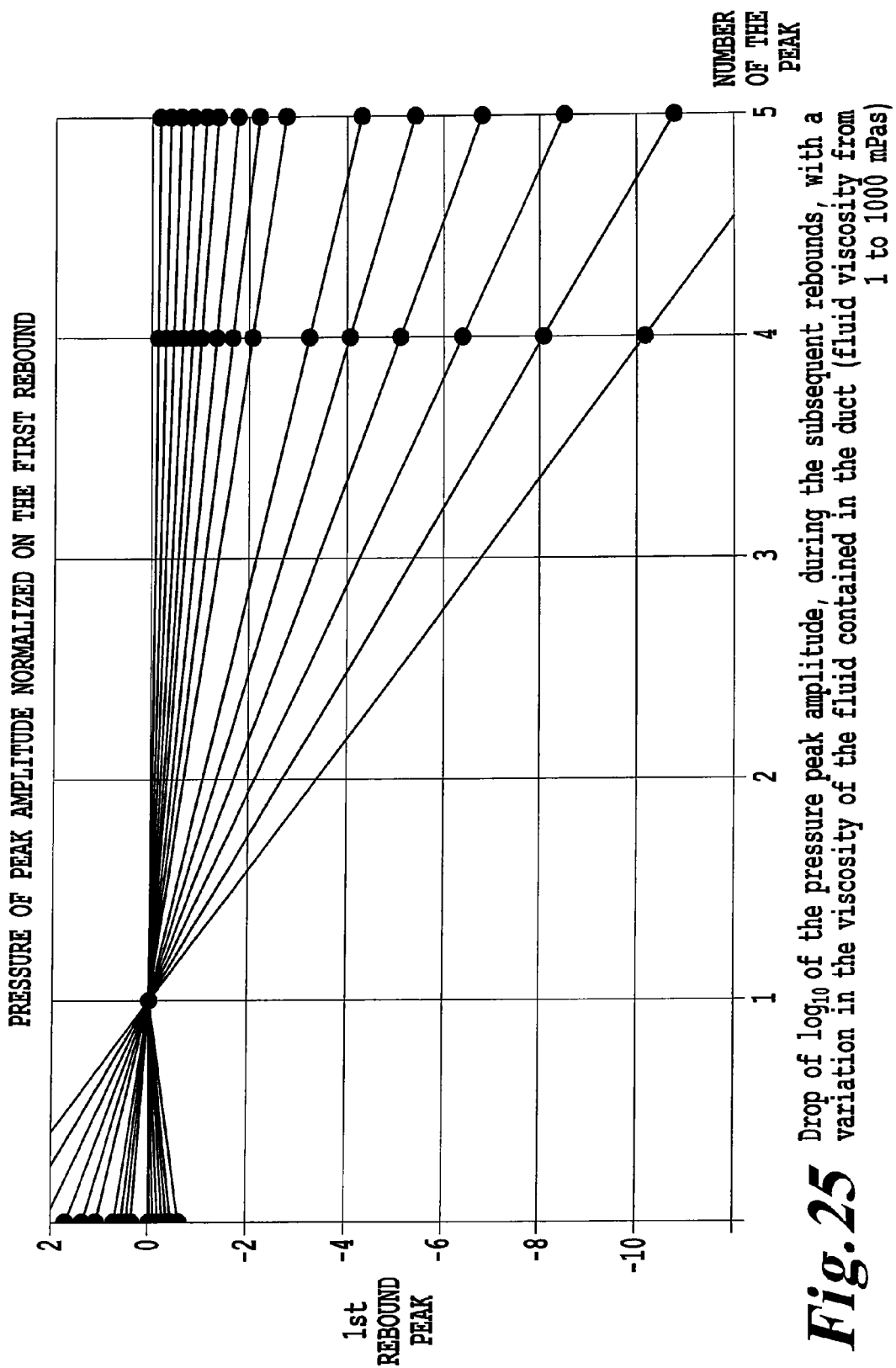
Fig. 25 Drop of $\log_{10}$ of the pressure peak amplitude, during the subsequent rebounds, with a variation in the viscosity of the fluid contained in the duct (fluid viscosity from 1 to 1000 mPas)

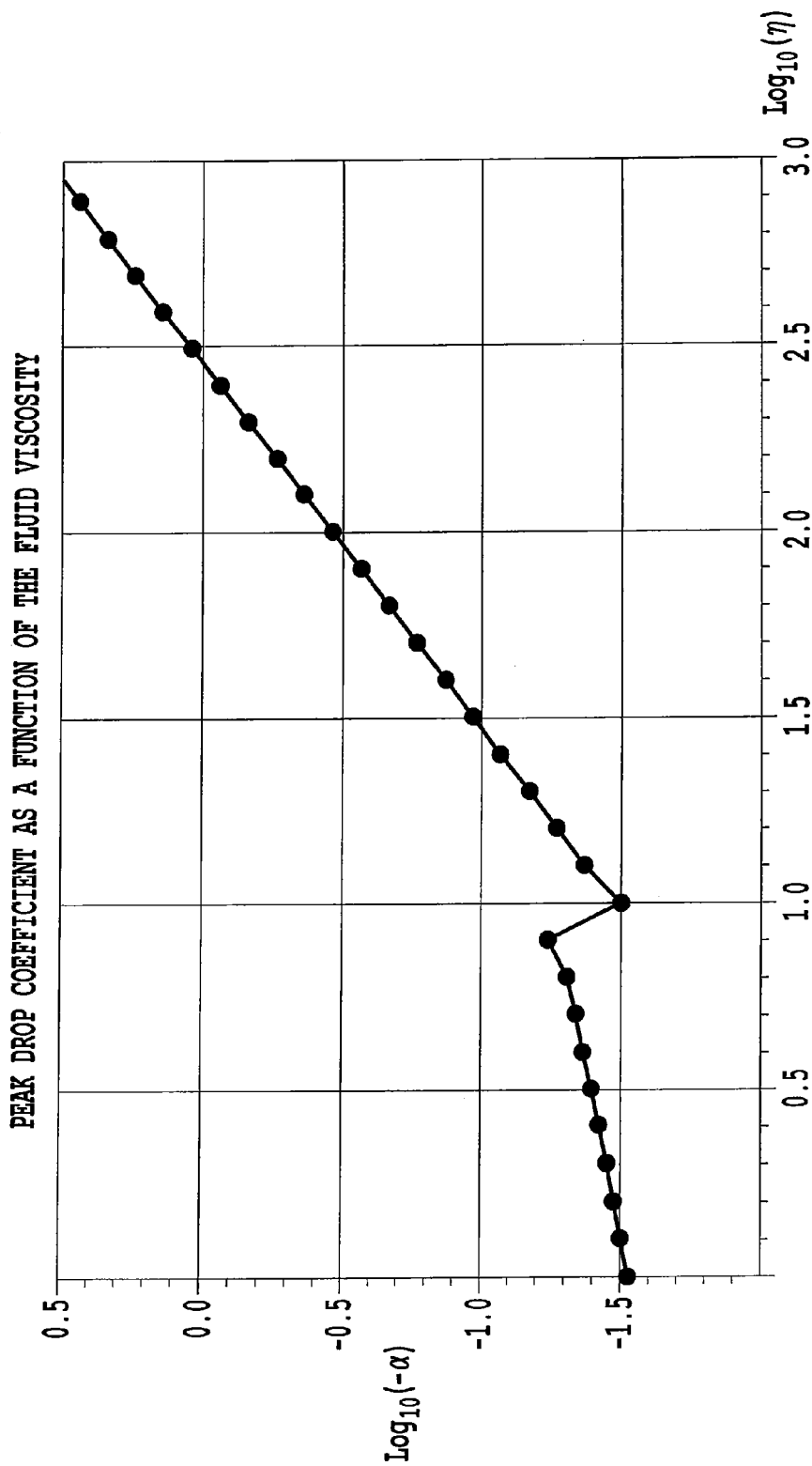
*Fig. 26* Relationship between the fading coefficient and the viscosity of the fluid contained in the duct: $\text{Log}_{10}(-\alpha)$ as a function of $\text{log}_{10}(\eta)$

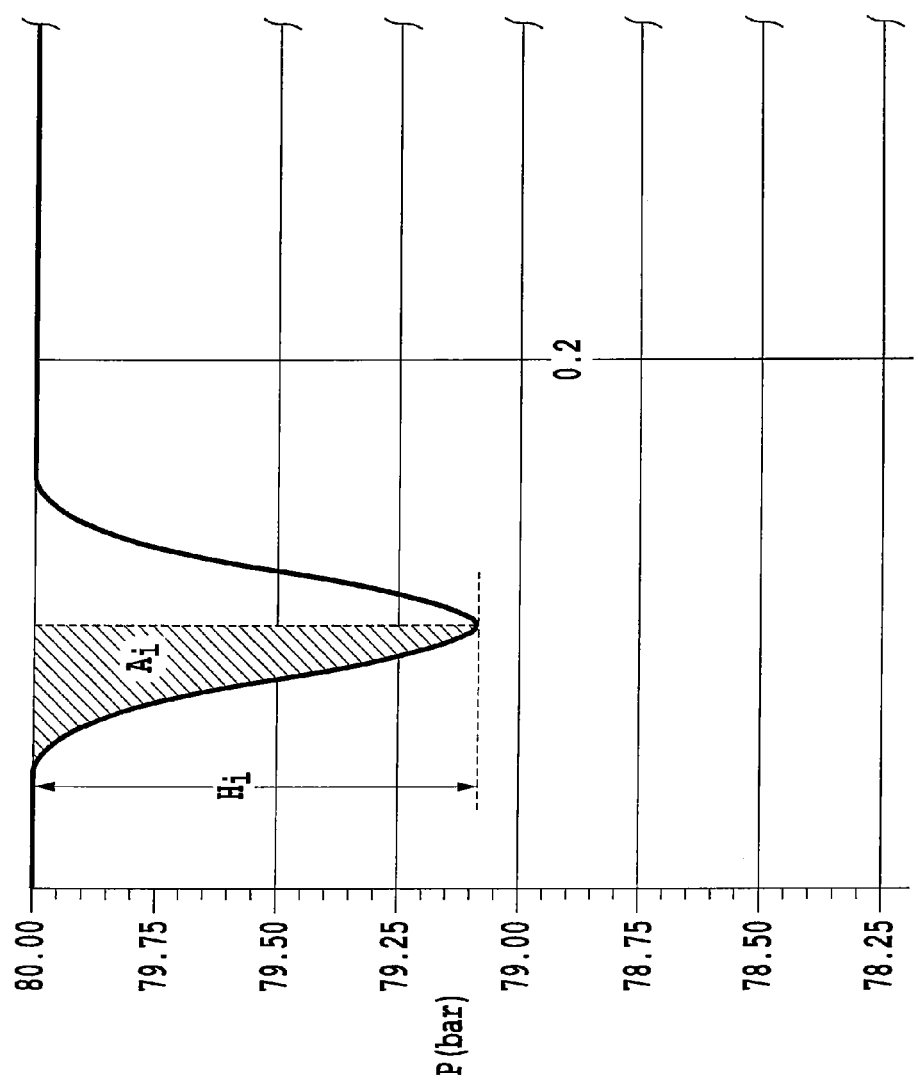
*Fig. 27* Substitution of the peak amplitude with the areas of the first half, in the case of the progressive widening of the peaks with the subsequent rebounds

PROCESS FOR REDUCING THE RESTART PRESSURE OF STREAMS SELECTED FROM WAXY CRUDE OILS, WATER-IN-CRUDE EMULSIONS AND DISPERSIONS OF HYDROCARBON HYDRATES The present application is a divisional application of U.S. Ser. No. 11/572,295 filed Jan. 18, 2007, now U.S. Pat. No. 7,896,020, the entire contents of which is incorporated herein by reference. U.S. Ser. No. 11/572,295 is a national stage of PCT/EP05/07819 filed Jul. 18, 2005. This application further is based upon and claims the benefit of priority from the prior Italy Patent Application No. MI2004A001480 filed Jul. 22, 2004.

BACKGROUND OF THE INVENTION

1. Field of the Invention

The present invention relates to a process for reducing the restart pressure of streams selected from waxy crude oils, water-in-crude emulsions and dispersions of hydrocarbon hydrates, at least partially structured.

2. Description of the Related Art

One of the aspects to be carefully taken into consideration during the development of an oil production plant, is to ensure a continuous and stationary flow of crude oil inside the ducts. Operation stops can occur for several reasons, from simple maintenance to unexpected situations (for example due to a pig block, or a breakdown in a plant for the treatment of crude oil). During the engineering stage, it is therefore necessary to carefully analyse all possible problems which can arise at the restart of production, above all for offshore pipelines (underwater pipes) which, due to their locations, are more difficult to have access to and are characterized by low temperature conditions (0-10° C.).

Structured system means a physical system having a high coordination between its units (molecules or aggregates of soluble or non-soluble molecules, also very extensive) produced by chemical and/or physical bonds. The coordination level depends on the number and strength of the bonds between the structural units. This situation generates an organization that resembles a network including the whole volume occupied by the system (for example a three-dimensional network of regular or amorphous crystals, of a gel, etc.).

The structural level of a substance can be expressed in terms of "yield stress", defined as the minimum stress (power per surface unit) to be applied to the substance so that this shows a permanent deformation and begins to flow. The "yield stress" is consequently a parameter strongly correlated with the stress (pressure difference at the ends of the pipe) to be applied to allow a stream to pass from a state of stillness to one of motion. The "yield stress" of a substance can be measured experimentally, for example by means of rotational rheometers. Other rheological parameters which allow the structural level of a substance to be quantified are the tensile modulus (G') and the dissipative modulus (G"). These material parameters are obtained through rheological measurements, effected in a low amplitude oscillatory system. These measurements consist in applying a sinusoidal deformation of variable (and/or constant) frequency and a sufficiently low amplitude as to not disturb the system ("An introduction to Rheology" H. A. Barnes, J. F. Hutton and K. Walters, Elsevier Science Publishers B.V., 1989). The response of the system to the stress will be a sinusoidal signal, out-of-phase with respect to that applied. From measuring the response signal intensity and from the entity of the phase displacement, it is possible to calculate two rheological parameters G' and G" which represent the elastic component (solid-type behaviour) and dissipative (liquid behaviour) of the system, respectively. In particular, the tensile modulus represents a parameter which quantitatively expresses (together with the viscosity and the "yield stress") the structuring degree of the stream considered ("Applied Fluid Rheology", J. Ferguson, Z. Kemblowski, Elsevier Science Publisher LTD, 1991).

As is well known from literature (A. Uhde, G. Kopp, "Pipeline problems resulting from the handling of waxy crudes", Journal of the Institute of Petroleum, vol. 57, number 554, 1971; C. Chang, D. V. Boger and Q. D. Nguyen, "Influence of thermal history on the waxy structure of statically cooled waxy crude oil", SPE Journal 5 (2) June 2000; C. Chang, D. V. Boger "The yielding of waxy crude oils", Ind. Eng. Chem. Res. 37, 1551-1559. 1998), during the progressive structuring of a fluid put in a state of rest, the "yield stress", the viscosity and the G' and G" modules change proportionally to each other. The two quantities are equivalent material parameters in representing the structuring degree of the stream. With reference to the problems relating to the restart of the stream, however, "yield stress" is the most representative parameter, as it directly expresses the threshold value necessary for generating the flow. Consequently, in the following text, reference will mainly be made to the "yield stress".

The above-mentioned streams are considered separately hereunder, with the purpose of outlining the specific problems relating to the restart of the duct.

Waxy Crude Oils

The presence of n-paraffins in crude oil can generate wax crystals at temperatures lower than a characteristic temperature of each crude oil, called WAT (Wax Appearance Temperature), which can be defined as the temperature at which the first crystals are observed. The Pour Point (PP), defined as the temperature below which an oil cannot flow under the force of gravity alone, due to its transformation into gel (solid-type behaviour), is found at temperatures lower than the WAT. In operative terms, the PP is measured according to the regulation ASTM D-97 and represents an empirical evaluation of the yield stress.

The WAT of many crude oils, like the PP, is higher than the temperature normally found in deep seabeds (2-3° C.) or in some geographical areas where onshore pipelines are installed.

Under flow-stop conditions, the gelation of crude oil at temperatures lower than the PP, creates a mass of gelled crude oil in a wide tract of the duct, which can generate serious drawbacks during the flow restart operations.

Industry is currently trying to prevent the problem of gelation by:

i) the installation, when possible, of lines and pumps capable of ensuring the necessary pressure in the case of a long and unexpected stoppage of the plant;
ii) the running of the plant, so as to reduce unexpected stoppages;
iii) the use of heated or insulated ducts, so as to reduce the heat exchange;
iv) the use of chemical additives and/or solvents which reduce the tendency or the rate of gelation of waxy crude oils, by improving the properties of the material in terms of viscosity and yield stress.

All these approaches however have various efficacy limitations, mainly in cases of unexpected and prolonged plant-stoppages, or they can be economically unsustainable for the development of the field (for ex. the use of heated pipes), due to the high investment and running costs. Furthermore, the problem can arise in fields already in production, which have been engineered without considering the possibility of the problem arising.

Water-in-Crude Emulsions

The formation of water-in-crude emulsions (defined as emulsions of the W/O type) creates a significant increase in viscosity with respect to the viscosity of the crude oil as such. The increase in viscosity of the water-in-crude emulsion is a function of the volume fraction of the water contained in dispersed form and can be described through relationships such as:

$$\eta_{relative} = \eta/\eta_S = (1 + 2.5\phi + 6.2\phi^2 + \ldots)$$

wherein $\eta$ is the viscosity of the emulsion (W/O), $\eta_S$ is the viscosity of the continuous phase (oil) alone, $\eta_{relative}$ is called relative viscosity and $\phi$ is the volume fraction of the dispersed phase (water).

It is also known that the increase in viscosity, being the same the fraction $\phi$ of the dispersed phase, also strongly depends on the particle-size distribution of the latter and on the nature of the interaction between the continuous phase (oil) and the dispersed phase. In the case of W/O emulsions formed with waxy crude oils, there is experimental and field evidence of significant and important increases in the relative viscosity and yield stress with a decrease in the temperature below the WAT of the oil. Under such conditions, serious problems can arise in the emulsion restart.

It is therefore necessary to intervene to reduce the viscosity and yield stress and consequently the restart pressure of these streams.

Dispersions of Hydrocarbon Hydrates

Hydrates are solutions in solid phase of water and other chemical species called guest molecules. The crystalline structure is produced by cages of water molecules (hence the name of clathrate products), in which the guest molecules are kept in a non-stoichiometric manner.

Hydrates can be formed at temperatures significantly higher than the formation temperature of water ice. For example, a 95:5 mixture of water and $C_1:C_3$ gaseous hydrocarbons, can form solid hydrates at temperatures slightly below 9° C. and at a pressure of 20 bar. It should be remembered that these operative conditions are not verified solely for particular climatic conditions (deep water and geographical positions with cold climates), but also in the presence of multiphase transport lines with high pressure drops: under these conditions, in fact, hydrocarbon gases generate deep cooling as a result of the Joule-Thomson effect.

The formation of hydrates is a relevant problem, as they can completely obstruct the production lines and, due to the complexity and dangerousness of the removal operations, can cause considerable delays in the production of hydrocarbons and consequently high economical losses.

The most common prevention systems of the formation of hydrates require the use of thermal inhibitors, such as methanol and glycol which, when added to the stream in concentrations equal to about 20% by volume with respect to the water present, lower the formation temperature of hydrates to values outside the operating range. This technique has drawbacks, however, in various production scenarios, among which deep water, due to the anti-economical treatment in the case of high volume fractions of water produced, and the necessity of minimizing plants for the separation and recycling of the thermodynamic inhibitor, mainly in deep water reserves.

Other prevention systems consist of kinetic inhibitors and anti-agglomerating products, prepared to be used at low dosages and disposable. These are chemical products capable of delaying the formation of hydrates or of mitigating their effects by forming hydrate dispersions less compact than the solid which would be formed without the addition of additives and therefore more easily pumpable to the pipeline. Kinetic inhibitors prove to be more advantageous with respect to the conventional techniques (isolated and/or heated lines and the use of methanol or glycol), both in terms of investment and operative costs, but they represent a technology which still has a poorly consolidated efficacy. It should also be noted that, in the presence of hydrate dispersions (formed thanks to the action of anti-agglomerating additives), long flow stoppages (several hours) can lead to significant increases in viscosity and yield stress in the same dispersions, as a result of which serious problems can arise at the re-start. Even in the presence of anti-agglomeration additives, it is therefore important to intervene to reduce the viscosity and re-start pressure.

A stream (whether consisting of waxy crudes, water/crude emulsions or hydrate dispersions, structured or partially structured) maintained under rest conditions and subject to cooling (until a fixed temperature, lower than the starting value, is reached) shows a progressive increase in the viscosity and yield stress which, after a time varying from a few hours to several days, reaches extreme values, characteristic of each stream.

SUMMARY OF THE INVENTION

It has been found that it is possible to facilitate the re-start of this stream by subjecting it to suitable mechanical stress, preferably induced by sound or ultra-sound or infra-sound frequencies.

In this way, it is possible to reduce, even by a few orders of magnitude, the viscosity and yield stress of the stream with respect to the values obtained in the absence of said stress. Furthermore, if the mechanical stress is applied during a sufficient period of time and intensity, the phenomenon remains even after interrupting the application, and the extreme viscosity and yield stress levels of the stream prove to be lower (at the reference temperature and pressure) with respect to those that would be reached in the absence of the above-mentioned stress.

The latter is the most significant element of the present invention: the fact that the reduction in the extreme viscosity and yield stress caused on the stream by the stress applied proves to be irreversible, provided the stress is applied for a sufficiently long time and has an intensity higher than a threshold characteristic of each stream.

The process, object of the present invention, for reducing the re-start pressure of streams selected from waxy crudes, water-in-crude emulsions and dispersions of hydrocarbon hydrates, at least partially structured, is characterized in that it applies, under flow-stop conditions, a mechanic stress on said stream, having:

for waxy crude oils and water-in-crude emulsions, temperatures lower than WAT (Wax Appearance Temperature), possibly, for these emulsions, lower than the Pour Point (PP);

for dispersions of hydrocarbon hydrates, at temperatures lower than the formation temperatures of said hydrates and at pressures higher than the formation pressure of said hydrates.

The intensity of the mechanical stress, regardless of its origin, is expressed hereunder by indicating the wall strain (shear stress) caused thereby, progressively along the pipeline during wave propagation.

Mechanical stress can be effected with different methods, among which flow rate and pressure waves, shear stress, gas insufflation, mixing with a suitable liquid having a different density with respect to the stream or shaking.

The mechanical stress can also be induced by sound, ultrasound or infrasound waves, which can be obtained through flow rate and pressure waves.

The first two types of stress represent examples of waves travelling along the pipeline and progressively exerting, on all the points of the fluid, a mechanical stress equivalent to wall stress. The latter magnitude is in direct correlation with the stress applied to a fluid by a rheometer, whether it be stress control or deformation. Therefore the quantitative information on the properties and behaviour of the streams in said measurement equipment can be expressed directly in the form of the intensity of the flow rate and pressure waves to be applied to the stream to obtain the desired stress values to the walls.

The desired effect can also be obtained by means of other types of stress, such as gas insufflation or mixing with another means having a different density. Their application modes however cannot be expressed directly in the form of a wall stress and therefore do not allow an "a priori" evaluation of their efficacy. They must consequently be applied on an empirical basis.

Hereinafter, the structure level (yield stress and viscosity) of the stream before the plant stoppage will be indicated with $\tau(t=0)$ and $\eta(t=0)$ (i.e. at time t=0, under typical conditions of T and P of the stream). After the stream stoppage, the flow is subjected to a progressive structuring process which causes the yield stress, in a time $t_{max}$, depending on the stream, to change from $\tau(t=0)$ to a maximum value, also typical of each stream, hereinafter named $\tau(t_{max})$.

The time $t_{max}$ for reaching the maximum structuring degree depends not only on the stream, but also on the evolution with time of the temperature and pressure. In general, an increase in the viscosity $\eta(t)$ and yield stress $\tau(t)$ corresponds to a decrease in a stream temperature. Even after reaching the equilibrium temperature however, the structuring of the stream can increase with time, due to internal reorganization processes, until characteristic extreme values called $\tau(t_{max})$ and $\eta(t_{max})$ are reached. For example, waxy crude oils, initially thermostat-regulated at a temperature $T_1$ higher than the PP of 30° C. and, subsequently, brought in 0.2 hr. to the temperature $T_2$ lower than the PP of 6° C., have reached the maximum structuring after 4 hours at the uniform temperature of $T_2$. Consequently, in these particular cases, $t_{max}$=4.2 h.

The reference process is shown in FIG. 1.

The stress must be applied after the stream stoppage (t≧0) and before the stream reaches the maximum structuring degree indicated with $\tau(t_{max})$ and $\eta(t_{max})$, due to the flow stoppage.

The energy to be supplied for irreversibly applying stress to the structure of the stream, changes, depending on its structuring level, and, in particular, increases with an increase in the structuring level. If the intensity of the stress applied is sufficient for the structuring conditions of the stream, then the structuring achieved by the stream due to the stress will be permanently lower than that which it would have reached in the absence of stress.

More specifically, by underlining the structure level $\tau(t)$ and $\eta(t)$ of the stream subjected to stress from the time $t_1 \geq 0$ to the time $t_2$, we then have:

$$\underline{\tau}(t \geq t_2) < \tau(t)$$

$$\underline{\eta}(t \geq t_2) < \eta(t).$$

In particular, the maximum reduction effect of the structuring can be obtained by applying the stress with continuity during times ranging from the stoppage time of the flow and $t_{max}$ or, preferably, the moment of re-establishing the flow conditions.

The stress must have a sufficient intensity with respect to the structuring degree of the stream at the initial time of application $t_1$, in order to produce a permanent reduction in the structuring level of the stream.

The intensity of the mechanical stress, regardless of its origin, is expressed hereafter by indicating the strain to the wall progressively caused thereby along the pipeline during the wave propagation.

The stress applied has an intensity sufficient for producing a permanent reduction in the structuring of the stream (viscosity and yield stress) when the wall strain is 15% higher, preferably 20% higher and less than 40%, than the specific yield stress of the stream at the starting moment of said stress.

BRIEF DESCRIPTION OF THE DRAWINGS

FIG. 1 is a stress graph for the reference process;

FIG. 2 is a stress graph for a waxy crude stream;

FIG. 3 is a stress graph for a water-in-crude emulsion stream;

FIG. 4 is a stress graph for a hydrate dispersion stream;

FIG. 5 is a graph showing variations in tensile modulus;

FIG. 6 is a graph of temperature variations in the tensile modulus of waxy crude;

FIG. 7 is a microphotograph under polarized light of paraffin crystals in a crude cooled through two different thermal profiles;

FIG. 8 is a graph showing stress variations in the viscosity of a waxy crude;

FIG. 9 is a graph showing shear stress variations in the viscosity of a waxy crude;

FIG. 10 is a graph showing stress variations in the viscosity of a waxy crude after one hour;

FIG. 11 is a graph showing stress variations in the viscosity of a waxy crude after four hours;

FIG. 12 is a graph showing frequency variation in tensile modulus in a waxy crude after four hours;

FIG. 13 is a graph showing frequency variation in tensile modulus in a waxy crude subjected to triangular sequences of shear rates, after four hours;

FIG. 14 is a graph showing time variation in tensile modulus in a waxy crude after four hours;

FIG. 15 is a graph showing frequency variation in tensile modulus in a waxy crude subjected to a constant shear rate, after four hours;

FIG. 16 is a schematic illustration of the equipment for generating the stress object of the invention;

FIG. 17 is a graph showing the instant flow rate trend produced using the equipment of FIG. 16;

FIG. 18 is a graph showing the wave rebound time on the other end of the duct;

FIG. 19 is a graph showing the maximum wall stress along the duct;

FIG. 20 is a graph showing the instant pressure evolution produced by the flow rate transient of FIG. 17;

FIG. 21 is a graph showing rebounds of the pressure peak of FIG. 20;

FIG. 22 is a graph showing changes in pressure with changes in duct inner diameter;

FIG. 23 is a graph showing changes in pressure with localized restrictions in duct inner diameter;

FIG. 24 is a graph showing changes in pressure with changes in viscosity;

FIG. 25 is a graph showing rebounds of changes in pressure with changes in viscosity;

FIG. 26 is a graph showing fading coefficient versus changes in viscosity; and

FIG. 27 is a graph showing peak amplitude in rebounds.

DETAILED DESCRIPTION OF THE PREFERRED EMBODIMENT

Examples of stress application to each type of stream for obtaining the effect claimed, are provided hereunder.
For the waxy crude stream: FIG. 2.
For the water-in-crude emulsion stream: FIG. 3.
For the hydrate dispersion stream: FIG. 4.
Examples for Waxy Crudes A reference waxy crude (paraffin) called A, was considered for studying the rheological properties of the paraffin gel (waxy) at a low temperature. The rheological properties of said crude were studied within a temperature range of 40° C. to 15° C. The minimum temperature (15° C.) is below the Pour Point of the crude (21° C. according to the regulation ASTM D97) thus ensuring the formation of a gel, representative of the specific phenomenon of interest.

The results of the rheological experimentation carried out on the crude A are indicated below. The results are proposed with the criteria of evidencing the effects of the main variables identified (cooling rate, minimum temperature and residence time at this temperature) on the consistency of the wax gel and then evaluating the reduction effect (irreversible) of the gel structuring (viscosity and yield stress) due to the application of shear stress.

In addition to the viscosity and yield stress, the tensile modulus (G') and dissipative modulus (G") values are indicated in this experimentation, effected using a stress control rheometer of Rheometric Scientific (DSR 200). This parameter will be used hereinafter together with the viscosity and "yield" for quantifying the structuring degree of the stream in question.

Influence of the Cooling Rate on the Consistency of the Wax Gel.

FIG. 5 shows the variations of G' (tensile modulus) and G" (dissipative modulus) when the temperature changes from 40° C. to 15° C. obtained by applying different cooling rates, from 0.05° C./min to 2° C. min. The measurements were taken at a constant frequency of 1 Hz and at a deformation range (0.15%) within the linear visco-elasticity range ("An introduction to Rheology", H. A. Barnes, J. F. Hutton and K. Walters, Elsevier Science Publisher B.V., 1989).

The experimental results obtained (se FIG. 5) show that the lower the cooling rate the higher the G' value is (and therefore of the gel consistency) measured at the minimum temperature of 15° C. This result is maintained with time, and this is a relevant aspect. FIG. 6 shows, as a confirmation of the above, the variations of G' in relation to the time (still at a constant frequency of 1 Hz and a small deformation amplitude) at the minimum temperature of 15° C. for the samples cooled down at different rates. Samples were monitored for over 16 hours after they had been cooled to 15° C.

The differences between the values of the G' modulus (and therefore of the consistency of the gel formed), measured at the end of the monitoring period of 16 hours, are comparable with the differences measured at the end of the cooling obtained with different thermal rates: the system memorizes the thermal rate with which it was cooled, in the structural characteristics of the gel at equilibrium.

The above-mentioned figures indicate the G' profiles only, as the G" profiles show the same behaviour at different levels.

A display of the structures formed following cooling to 15° C. through different thermal rates and after waiting 4 hours for thermal equilibrium, was obtained by means of optical microscopy under polarized light (see FIG. 7): by applying a very low rate (0.05° C./min), the paraffin crystals have time to organize themselves in correspondence with nucleation centres, forming "islands" of larger dimensions with respect to those obtained at a much higher rate (2° C./min) where the system has no time for organizing itself. In this latter case the network formed is much more uniform but thinner and, above all, mechanically weaker. This is the reason why the tensile modulus value and, therefore the viscosity and yield stress of the system at equilibrium, obtained by means of a lower cooling rate, is higher than that obtained at a higher rate.

Influence of the Minimum Temperature on the Consistency of the Wax Gel.

Viscosity measurements were carried out on the basis of the above observations, at temperatures ranging from 40° C. to 15° C., in relation to the stress applied. The purpose was to evaluate the viscosity and yield stress variation as a function of the temperature.

The crude under consideration (A), see FIG. 8, shows, at temperatures ranging from 40° C. to 30° C., a sharp transition between a Newtonian behaviour (constant viscosity and regardless of the stress applied and yield stress null) and non-Newtonian of the pseudo-plastic type (the viscosity decreases with an increase in the stress applied and the yield stress has positive values). The yield stress value is obtained from the viscosity vs stress curves shown in FIG. 8, as the stress at which the viscosity has a sharp reduction (2 or 4 orders of magnitude). Table I shows the dependency of the yield stress, the viscosity at zero shear and the viscosity at high shear ($\eta_\infty$) on the temperature for crude A. FIG. 9 shows a typical profile viscosity vs stress indicating the parameters which characterize the gel state, i.e. $\tau_y$, $\eta_0$ and $\eta_\infty$.

TABLE I

| T (° C.) | $\tau_y$ [Pa] | $\eta_0$ [Pa·s] | $\eta_\infty$ [Pa·s] |
|---|---|---|---|
| 40 | 0 | 0.065 | 0.065 |
| 30 | 0.2 | 3460 | 0.103 |
| 25 | 1.7 | 5890 | 0.136 |
| 20 | 18.6 | 3.55E+5 | 0.233 |
| 15 | 63.4 | 3.31E+6 | 0.304 |
| 10 | 233 | 3.54E+7 | 0.304 |

Influence of the Residence Time (Soak Time) on the Consistency of the Wax Gel.

The effect of the soak time was evaluated on the consistency of the wax gel at temperatures of 15° C. and 20° C.

The result of the experimentation shows that with an increase in the soak time at a certain temperature, there is an increase of the gel consistency (increase in the yield stress value). FIGS. 10 and 11 show the flow curves obtained by imposing a waiting time of 1 and 4 hours; the relevant yield stress values are shown in TAB II.

Significant increases in the gel consistency were no longer measured for waiting times of over 4 hours. Also in this case, it can assumed that the effect of the soak time on the gel consistency is reduced with a decrease in the equilibrium temperature.

TABLE II

| T [° C.] | $\tau_y$ after 1 hr [Pa] | $\tau_y$ after 4 hr [Pa] |
|---|---|---|
| 20 | 10 | 20 |
| 15 | 54 | 68 |

Once the "fundamental rheological" behaviour of the crude with a decrease in temperature had been identified, the possibility of intervention on the formation kinetics of the wax gel, through mechanical stress, was evaluated, in order to reduce its consistency at thermal equilibrium.

Example 1

Influence of the Shear History on the Wax Gel Consistency.

After verifying that after 4 hr at 15° C. of the crude A, the gel formed does not show any signs of further increase in its consistency (G' constant and yield stress constant under these conditions) the influences were evaluated of suitable stress on the tensile modulus G' and of the yield stress of the gelled crude. Different shear histories to which the gel was subjected at a temperature of 15° C. are indicated below.

i) Unperturbed Gel at Equilibrium

A measurement was effected on the crude cooled to 15° C. and left unperturbed for 4 hours, at a low shear amplitude, of the modules G' and G" with the variation in frequency (see FIG. 12). Under these conditions, the gel shows a module G' value at 1 Hz (6.28 rad/s) equal to 4,700 Pa and a yield stress value equal to 63.4 Pa. These parameters represent the measurement of the consistency degree of the gel of crude A obtained under unperturbed conditions at 15° C.

ii) De-Structured Gel at Equilibrium

A rate sweep sequence (from $0.1\ s^{-1}$ to $1000\ s^{-1}$) is applied to the crude gelled in item i), it is then left to restructure for 4 hours at 15° C., following the variation of G' over a period of time. Once equilibrium has been reached (G' reaches a plateau value with respect to the time), a measurement in oscillatory regime is carried out, at a small shear amplitude, to measure G' and G" with the variation in the frequency (see FIG. 13). The result of this measurement is a G' value equal to 1200 Pa and this means, when compared with the unperturbed gel values at equilibrium, a reduction of about 70%. It should be noted that the value of G', during the time the shear is applied, drops by 1-2 orders of magnitude; the energy required for moving the gelled crude is therefore minimum during and immediately after the application of the mechanical stress.

iii) Perturbed Gel During Cooling:

The crude is subjected to shaking during cooling from 40° C. to 15° C. Two different stress rates were applied in order to obtain the shaking: $1\ s^{-1}$ and $50\ s^{-1}$. Once the temperature of 15° C. has been reached, the sample is left to restructure for four hours, following the variation of G' with time (FIGS. 14 and 15). The result of this measurement shows an average value of the module G' equal to 1700 Pa if the cooling was effected by shaking at a shear rate of $1\ s^{-1}$ and 1500 Pa, if the cooling was effected by shaking at a shear rate of $50\ s^{-1}$. By comparing these values with those of the unperturbed gel at equilibrium, a reduction of about 70% is still observed. Table III shows the results relating to the influence of the different stress histories on the consistency degree of the gel, expressed in terms of tensile module G' and yield stress, compared with the values measured of the unperturbed system (percentage variation).

TABLE III

| Unperturbed G' [Pa] | G' [Pa] after sequence rate (see text) | G' [Pa] after cooling effected with shear rate of $1\ s^{-1}$ | G' [Pa] after cooling effected with shear rate of $50\ s^{-1}$ |
|---|---|---|---|
| 4700 | 1200 | 1700 | 1500 |

| Unperturbed yield stress [Pa] | yield stress [Pa] after rate sequence (see text) | yield stress [Pa] after cooling effected with shear rate of $1\ s^{-1}$ | yield stress [Pa] after cooling effected with shear rate of $50\ s^{-1}$ |
|---|---|---|---|
| 68 | 10 | 27.2 | 23.8 |

Examples for Water/Crude Emulsions

A reference crude called B, emulsified with water percentages ranging from 1% to 2%, was considered for studying the rheological properties of a water-in-crude emulsion. The rheological properties of said emulsion were studied within a temperature range of 40 to 15° C. The minimum temperature considered (14° C.) proved to be above the crude Pour Point temperature (−6° C.) (determined following the regulation ASTM D97): at this temperature the formation is measured of a particularly viscous gel, and this justifies the considerable pumping problems in the plant.

The results of the rheological experimentation on the emulsion of crude B in water are indicated below. The results are shown in order to demonstrate the influences of the main variables (minimum temperature, residence time) on the consistency of the crude-in-water emulsion.

Example

Influence of the shear history on the consistency of the water-in-crude emulsion.

Having verified that, after leaving the crude B emulsion at 12.5° C. for 3 hours, the gel which was formed does not show any signs of a further increase in the consistency (G' constant and yield stress constant under said conditions), the influence of suitable "shear/stress" histories was evaluated on the values of the tensile module G' and yield stress of the gelled crude. Several shear histories are indicated below, at which the gel was subjected at a minimum temperature of 15° C.

i) Unperturbed Gel at Equilibrium.

A measurement in an oscillatory regime, at a low shear amplitude was effected on the water-in-crude emulsion, which was cooled to 15° C. and left unperturbed for 4 hours, to measure the modules G' and G" with the variation in frequency. Under these conditions, the gel shows yield stress values equal to 250 Pa. This parameter represents the measurement of the consistency degree of the gel of the emulsified crude B obtained under unperturbed conditions at 15° C.

ii) De-structured Gel at Equilibrium

The gelled crude of item i), after being cooled to 15° C. and left unperturbed for 4 hours, is "de-structured" by applying a rate sweep sequence (from $0.1\ s^{-1}$ to $1000\ s^{-1}$), it is then left to restructure for 4 hours at 15° C., following the variation in G' over a period of time. Once equilibrium has been reached (G' reaches a plateau value with respect to the time), a measurement is carried out under stress control. The result of this measurement shows a yield stress value equal to 10 Pa which, compared to the values of the unperturbed gel at equilibrium, shows a reduction of about 98%; the energy required for moving the gelled crude is therefore minimum during and immediately after the application of the mechanical stress.

iii) Perturbed Gel During Cooling:

The crude undergoes shaking while it is cooled from 40 to 15° C. Two different shear rates were applied to obtain the shaking: 1 s$^{-1}$ and 50 s$^{-1}$. Once the sample has reached a temperature of 15° C., it is left to restructure for 3 hours, following the viscosity variation with stress (FIG. 10). The result of this measurement shows a yield stress value equal to 1 Pa, if the cooling was effected by shaking with a shear rate of 1 s$^{-1}$, and 0 Pa if the cooling was effected by shaking with a shear rate of 50 s$^{-1}$. By comparing these values with those obtained on the unperturbed gel at equilibrium, a further reduction is observed equal to about 100%.

Table IV shows the results relating to the influence of the different shear histories on the consistency degree of the gel, expressed in terms of yield stress, by comparison with the values measured for the unperturbed system (percentage variation)

TABLE IV

| Unperturbed yield stress [Pa] | Yield stress [Pa] after rate sequence (see text) | yield stress [Pa] after cooling effected with shear rate of 1 s$^{-1}$ | Yield stress [Pa] after cooling effected with shear rate of 50 s$^{-1}$ |
|---|---|---|---|
| 250 | 10 | 1 | 0 |

Examples for Hydrate Dispersions

A mixture of crude (crude C), water (20% volume) and methane was considered for studying the rheological properties of a dispersion of hydrates. This mix was studied by using a stress control rheometer (DSR 200 of Rheometric Scientific), equipped with a pressure cell capable of operating at up to 140 bar. The rheological characterization was carried out, with reference to the PVT data of the mix considered, at a pressure and temperature corresponding to the formation of the hydrate. The addition of an anti-agglomeration kinetic inhibitor (polyvinyl pyrrolidone, PVP) causes the formation of a dispersion of hydrates which, if left unperturbed at the formation temperature of the hydrates, increases its structuring degree, causing the blockage of the pipeline. It is therefore necessary to intervene using the techniques proposed for reducing the structuring degree (thus the viscosity and yield stress) of the dispersion.

Table V shows the results relating to the influence of the different shear histories on the gel consistency degree, expressed as yield stress, by comparison with the values measured for the unperturbed system (percentage variation).

TABLE V

| Unperturbed yield stress [Pa] | Yield stress [Pa] after rate sequence (see text) | yield stress [Pa] after cooling effected with shear rate of 1 s$^{-1}$ | Yield stress [Pa] after cooling effected with shear rate of 50 s$^{-1}$ |
|---|---|---|---|
| 300 | 150 | 210 | 190 |

A method is now described, which can be used both for the stress of a liquid present in a pipeline, with the aim of irreversibly reducing its structuring, and for monitoring the structuring process, by measuring the instant viscosity of the liquid present in the pipeline and observing the possible formation of occlusions, restrictions or variations in the inner profile of the duct.

The method, which is a further object of the present invention, for measuring the profile of the inner diameter of a pipe and the instant viscosity of the fluid contained therein, is characterized in that it is carried out by the generation of sound or infra-sound waves produced, under flow absence conditions, by means of fast flow-rate transients, which are then registered by a suitable measuring device and processed, thus obtaining the profile of the inner diameter of the duct and the instant viscosity of the fluid contained therein.

In the text, repeated reference will be made to the illustrative situation of a duct 10 km long, having a uniform inner diameter of 0.3048 m (12"), uniform roughness equal to 20 microns and a variable altimetrical profile with horizontal and vertical tracts, as is typical of offshore transport lines. It should be noted that the inclination of the duct has no influence on the techniques illustrated which can therefore also be used in oil wells. A liquid is contained in the duct, having a bubble pressure equal to 70 bar and under single-phase non-structured conditions, a density and viscosity of 10 cP. The duct pressure is assumed as being higher than the bubble pressure in each point, to avoid the formation of pipe regions predominantly or completely occupied by the gas. The flow rate wave propagation rate and pressure is equal to 1,200 m/s. The data are summarized in the following table.

| Oil | |
|---|---|
| ρ density (constant along the duct) | 0.85 g/cm$^3$ |
| Viscosity under regular flow η conditions | 10 mPas |
| Bubble pressure | 70 bar |

| Duct | |
|---|---|
| Duct length L | 10,000 m |
| Inner diameter of the duct D | 0.3048 m (12") |
| Roughness ε | 20 microns |
| Minimum pressure along the duct | 80 bar |

| Transients | |
|---|---|
| propagation rate c | 1,200 m/s |

Generation and Measurement Equipment of Flow-Rate Transients.

The techniques for generating stress and for measuring the fluid structuring and duct diameter mentioned below, are based on the fact that a temporary discharge or admission of fluid in the duct generates a flow-rate and pressure wave which propagates along the duct at a rate approximately equal to the sound rate in the fluid. The exact propagation rate of the wave is, in fact, a function of several parameters, among which the sound rate in the non-confined fluid, the elasticity of the duct walls and the spectrum of the frequencies contained in the wave itself, and can be directly measured as illustrated below. Its a priori knowledge is therefore not necessary for the application of the method.

The temporary discharge of liquid can, for example, be caused, in a simple and reproducible way, with the help of the equipment shown in FIG. 16. In said equipment, the sphere valve A, which is in contact with the duct fluid at the pressure P$_1$, is rapidly opened, manually or through a fast-acting servomechanism, so as to put the duct in communication with the container having a volume V, which is at a pressure of P$_2$, different from $P_1$. The pressure difference therefore induces a liquid flow between the duct and the recipient which, in a time period of T, becomes completely exhausted due to the reestablishment of the equilibrium conditions $P_1$ and $P_2$. The most common embodiment of this equipment contemplates the container C being at atmospheric pressure before the opening of valve A.

For the repetition of the generation of the transient, it is sufficient to close valve A, open valve B, restore the initial pressure conditions of the container between the two valves and to close valve B. In the most common embodiment, this operation consists of the complete or partial emptying of the container, allowing the fluid to be discharged.

For all the examples provided below, it is assumed that the volume of the container C is equal to 0.35 It and that the flow-rate transient generated by the sudden opening of valve A is that illustrated in FIG. 17.

The trend is representative of that obtained during the field test. A corresponding pressure transient, which can be registered by means of the system M for the pressure measurement, is associated with the flow-rate transient produced by the equipment of FIG. 16. The presence of said pressure measurement system is not necessary for generating the de-structuring stress of the fluid, but it is necessary to register the pressure waves generated and their subsequent rebounds, with the aim of investigating the state of the fluid and the piping illustrated below.

The relative position of the measurement equipment M and the equipment for the generation of transients G, has no particular importance. Should the analysis methods described below be applied, it would be appropriate to have the apparatus G at a short distance (max. 5 meters) from the interception valve.

The frequency spectrum contained in the impulse generated by means of the equipment G is prevalenty lower than the sound limit (16 Hz) and therefore no audible sound is associated with the transient. Furthermore, the low frequency of the spectrum favours the high propagation distance of the signal, as the components having a progressively higher frequency diminish more and more rapidly with an increase in the distance covered, and limit the packet dispersion, maintaining the transient width unaltered for a long period of time. During tests on real pipelines, it was found out that the pressure wave generated by means of the equipment of FIG. 1 is capable of covering considerable distances (even many hundreds of Km) and of rebounding numerous times on the closed valves at the end of the pipeline, before completely diminishing due to dissipative phenomena.

The equipment of FIG. 1 can be used (1) for determining the real profile of inner diameters of the duct after its closing, (2) for applying the de-structuring stress object of the present invention, to the fluid (3) for repeatedly measuring the viscosity of the fluid contained, keeping the structuring process under control, (4) for detecting in real time the possible formation of solid matter in the pipeline, for example hydrates, or other important variations in the fluid properties. All this information can be obtained through the analysis procedures illustrated below.

First of all, a simulator will be described, capable of reproducing the behaviour of the flow-rate waves and pressure along the pipeline. The use of the simulator is not essential for the simple application of the de-structuring stress, but it can significantly contribute to the measuring of the container C of the equipment for the transient generation, and it is essential for the application of the measurement methods of the diameter profile and viscosity. The optimal mode for the application of the destructuring stress will be described further on.

Finally, the procedures will be described for obtaining the diameter profile immediately after the closing of the duct, and for testing the fluid viscosity and other useful information for keeping the structuring process under control.

Flow-Rate Wave Simulator and Pressure

A simulator is essential for a correct analysis of the pressure data recorded by the measurement system M (See FIG. 16) and must be capable of reproducing the pressure wave and flow-rate evolution, induced by the manoeuvre effected on the valve A of the equipment of FIG. 16. The choice of simulator is not binding but, for the sake of clarity, one is described below which has proved to be capable of reproducing the desired phenomena.

The equations used by the simulator are the following:

$$\frac{\delta p}{\delta t} + \rho c^2 \frac{\delta v}{d\xi} = 0 \tag{1}$$

$$\rho \frac{\delta v}{\delta t} + \frac{\delta p}{d\xi} = -\Phi(v, D) \tag{2}$$

$$\Phi(v, D) = \frac{f(Re)}{D} + \rho \frac{v|v|}{2} \tag{3}$$

$$Re = \frac{|v|D\rho}{\eta} \tag{4}$$

$$p = p(t, \xi) + \rho g z(\xi) \tag{5}$$

in which $p(t,\xi)$ represents the difference between the pressure at position $\xi$ along the pipeline and the corresponding hydrostatic pressure:

$$p(t,\xi)=p_{real}-\rho g z(\xi) \tag{6}$$

and:

$\xi$ is the space curvilinear coordinate along the pipe
D is the pipe diameter
$z(\xi)$ is the elevation of the point in position $\xi$
Re is the Reynolds number, defined by (4)
c is the sound velocity in the liquid
f is the friction factor, depending on Re
g is the acceleration due to gravity
t is the time
v is the liquid velocity in the pipeline
$\eta$ is the liquid viscosity
$\rho$ is the liquid density
$\phi$ is the function defined in equation (3).

PM indicates the pressure measured by the measuring system M of FIG. 16. Hereinafter, with no limitations, M is presumed to be placed at one end of the pipeline, i.e. just before one of the interception valves.

For the numerical resolution, the pipeline is ideally divided into a wide number of elements $E_n$, with n=1 . . . N, consisting of two halves of the same length inside which the roughness and diameter values are constant. The elements have a length of $$\lambda = \frac{\delta t \, c}{2} \tag{7}$$

wherein $\delta t$ is the sampling interval of the pressure measurements in the measuring point PM.

Any $E_n$ element is in the average position $z_n$ which is $$z_n = n\lambda - \lambda/2 \tag{8}$$

and has two diameters $D_n^{up}$ and $D_n^{down}$ and two roughness values $\epsilon_n^{up}$ and $\epsilon_n^{down}$, associated with the upper and lower halves, respectively.

Possible diameter changes can only take place inside each element. Consequently, the parameters relating to the lower part of each element are the same as that relating to the upper part of the following element:

$$D_n^{down} = D^{up}_{n+1} \tag{9}$$

$$\epsilon_n^{down} = \epsilon^{up}_{n+1} \tag{10}$$

The number N of the elements, each of them having a length of λ, is given by:

$$N = \frac{\Delta t_R}{\delta t} \tag{11}$$

wherein $\Delta t_R$ is the time between the transit and its rebound at the other end of the pipe, as illustrated in FIG. 18.

By indicating with $A_n^{up}$ and $A_n^{down}$ the areas of the upper and lower sections of each element, in the elements in which the upper diameter is different from the lower diameter, the following equation is used:

$$v_n^{up} A_n^{up} = v_n^{down} A_n^{down} \tag{12}$$

which represents the inflow and outflow balance of the element.

The initial conditions for the resolution of the system of equations are given by the pressure profile under steady conditions, calculated for each element starting from the measuring point M, by using the equations for the pressure drops containing the Fanning friction factor and an empirical equation for the calculation of the friction factor, such as, for example, the Colebrook formula (Colebrook, J Inst. Civ. Eng. [London], 11,133-156 1938-39).

The boundary conditions for the resolution of the equation system are given by the fixed (and constant) value of the pressure at the end of the pipe where the flow rate transient is applied before the beginning of the closing operation $$p(t,0) = po \tag{13}$$

and by the evolution of the flow rate at the end of the pipe during the transient generation:

$$Q(t, 0) = \begin{cases} 0 & t \leq 0 \\ f(t) & 0 < t \leq \Delta t_{trans} \\ 0 & t > \Delta t_{trans} \end{cases} \tag{14}$$

The equations are solved using the method of characteristics, as described, for example, in D. Barba, Electronic calculation in the chemical engineering—Siderea, Rome, 1971.

In addition to the geometrical description of the well, the initial and boundary conditions and the variables linked to the discretization (number of elements), the following data must also be provided at the simulator inlet:

The time span dt of the simulation, defined by the formula $dt = \delta t/2$ and the total time $t_{sym}$ during which the simulation is carried out.

The flow rate evolution Q(t) made discrete according to the time span of the simulation:

$$\begin{cases} Q(n dt) & 0 \leq n \leq \Delta t_{trans}/dt \\ Q(0) = 0 \\ Q(\Delta t_{trans}/dt) = 0 \end{cases} \tag{15}$$

wherein $\Delta t_{trans}$ is the time span between the beginning of the transient (t=0) and the end of the transient.

The value c of the sound velocity in the liquid, assumed as constant along the pipe and calculated, after the first transient generation, by dividing the double of the line length by the time between the pressure peak generated and its rebound on the other end of the duct, as illustrated in FIG. 18. The values of the transient velocity propagation in pipes containing hydrocarbons, vary within the range of 1,000-1,300 m/s.

An estimation of the viscosity values, diameter and roughness for an initial tract of the pipe, from the measuring point of a length (measured along the pipe) ξ, whose value can be estimated starting from the sound velocity c and from the measurement of the time span between the maximum of the pressure transient peak and its end, as illustrated in FIG. 18:

$$\xi = c \Delta t_p / 2 \tag{16}$$

The characteristics of the pipeline for a distance ξ from the measuring point, as well as those of the fluid contained therein, cannot be obtained from the methods explained herein. In practice, this does not represent an important limit, as the equipment of FIG. 1 allows transients to be generated for which $\Delta t_p = 0.04$ s and therefore ξ varies within the range of 20-26 m for velocities c ranging from 1,000 to 1,300 m/s.

A diameter D(ξ) and roughness ε(ξ) profile of the pipe, according to the discrete sectioning of the pipe defined above. If these are not known, for example due to the presence of deposits which have altered, in a way that cannot be defined "a priori", the inner diameter of the duct, the inner diameter profile and an average (constant) value of the roughness can be obtained through methods which will be exposed hereunder. Therefore, in correspondence with each element $E_n$, the following are defined:

$$D_n^{up} e D_n^{down} \tag{17}$$

$$\epsilon_n^{up} \text{ and } \epsilon_n^{down} \tag{18}$$

The pressure value in the measuring point at time 0, corresponding to zero flow rate:

$$PM(t=0). \tag{19}$$

Once the inlet data have been provided, the following can be obtained with the simulator:

The evolution of the velocity profile $v_n^{up}(n\,dt) = v_n^{down}(n\,dt)$ with n=0 ... $t_{sym}/dt$.

The evolution of the profile of the pressures $P_n(n\,dt)$ in the central point of each element $E_n$ and, in particular, the pressure evolution in the measuring point $PM = P_1$.

Application of De-structuring Waves to the Fluid

Following the generation of the flow rate and pressure wave by means of the equipment of FIG. 16, illustrated in FIG. 20, all of the ξ points of the pipeline through which the wave passes, are also subjected to wall stress, expressed by σ(ξ, t). From the moment of the transient generation, the maximum value of the wall stress caused by the same in all points of the pipeline is given by:

$\sigma_{max}(\xi) = Max(\sigma(\xi,t)$ for times $t$ subsequent to the transient generation.

In words, $\sigma_{max}(\xi)$ represents the maximum wall stress generated, in each point of the duct, by the flow rate transient generated with the help of the equipment of FIG. 16.

The present invention indicates that the stress will produce an irreversible effect on the fluid during its structuring, on the condition that $\sigma_{max}(\xi) > \tau(\xi, t)$, wherein t, in this formula, stands for the time span between the stoppage of the fluid and the wave passage and $\tau(\xi, t)$ is the yield stress of the fluid present in position $\xi$ of the duct at time t.

The maximum value of the wall stress caused by the perturbation, can be calculated in different ways for each pipeline. An example will be provided hereunder, in which this calculation is effected with the help of the fluid dynamic simulator of transients described in the following paragraph. In the case of the example, the flow rate transient illustrated in FIG. 17 generate the wall stress $\sigma_{max}(\xi)$ along the pipe illustrated in FIG. 19, for three different values of the viscosity of the fluid present in the duct: 10 cP, 100 cP and 1,000 cP.

When this fluid is a waxy crude having, at time t, a yield stress of 5 Pa, then the transient thus generated is capable of generating a permanent de-structuring effect on the fluid itself. If this stress is not sufficient with respect to the fluid present in the duct, it is possible to increase the volume V of the container C, with the same filling time, so as to increase the wall stress value, until the desired de-structuring effect is obtained.

As mentioned before, with the equipment illustrated in FIG. 16, the propagation phenomenon of the pressure waves generated in the fluid, can also be used to determine the evolution with time of the viscosity of the fluid present in the duct. For this purpose, it is possible to use the analysis method of the pressure signals registered by the system M presented hereunder.

In this way, the equipment illustrated in FIG. 16 can be applied to generate stress which reduces the structuring of the fluid, and to measure the evolution with time of its viscosity and, therefore, to control the entire process.

Measurement of the Profile of the Inner Diameters of the Duct.

The flow rate transient thus generated induces an evolution of the pressure, measured, for example, near the production point of the transient, analogous to that illustrated in FIG. 20. The course of the pressure shown in the figure, was obtained using the simulator described in the specific paragraph and it is representative of the actual behaviour in the pipeline. In the example, the pressure in the measuring point, in a stop condition, is assumed as being equal to 80 bar.

The pressure peak generated with the equipment of FIG. 16, by propagating along the duct, in addition to generating the local stress which represents the object of the present invention, can partially or completely rebound on possible obstacles, diameter variations of the duct or fluid non-homogeneity. In the case of a uniform fluid in a duct with a uniform real diameter, the signal rebounds on the other end of the closed line and return to the measuring point. Real diameter means the diameter actually available to the fluid, due to the pipeline and to possible deposits therein.

These rebounds are repeated until the signal is gradually exhausted, as illustrated in FIG. 21.

It should be noted that the amplitude of the first rebound can, in general, be even larger than the first impulse generated. The amplitude of the different rebounds, i.e. their attenuation, depends on several factors, among which the viscosity of the fluid contained in the duct.

In general, any sudden change in the real inner diameter of the duct, or pipe roughness, or again in the viscosity or density of the fluid contained therein, causes the partial or complete rebounding of the wave generated, and can be detected by analysing the pressure signals recorded by the measuring equipment M of FIG. 16.

With reference to the example duct, FIG. 22 shows the signal associated with a change in the inner diameter of the duct with an expansion equal to 0.002 m situated at 500 m from the transient generation point. Again as an example, FIG. 23 shows the signal associated with a localized restriction (length 1 m) of the inner diameter of the duct equal to 0.002 m situated at 500 m from the transient generation point. Experiences on real pipes show that both examples illustrated in the figure are realistic and that the characteristics indicated can be found in practice.

Experience shows that, even when the wave set undergoes a progressive widening, due to dispersion phenomena which induce components having a different frequency to propagate in the pipeline at different speeds, the qualitative analysis techniques of the signal remain unaltered, whereas quantitative analyses would require the use of a simulator capable of reproducing the dispersion phenomena. The simulator shown in the text is not capable of performing this function.

Duct with a Changeable Real Inner Diameter

Real diameter means the diameter actually available to the fluid, due to the pipeline itself and to possible deposits therein.

A method is described hereunder which is useful for quantifying the real inner diameter of a duct and the viscosity profile of the fluid contained therein, starting from the pressure data recorded by the equipment of FIG. 1. The method can be applied to any pipe, regardless of its inclination, provided it contains a liquid and does not have gas pockets which almost completely or completely occupy some of its tracts. If some free gas is contained in the duct, as in the case of an oil under a pressure lower than its bubble pressure, before applying these methods, it is necessary for the pressure in all points of the duct to be increased above the bubble pressure, for example by injecting small amounts of liquid into the duct or, in the case of a well, by reducing its flow rate supply. If these manoeuvres are not completely effective, it should be considered that small amounts of free gas could be interpreted as expansions of the inner diameter. Higher quantities of free gas, on the contrary, could have a negative influence on the propagation of the flow rate and pressure transients, thus limiting the efficacy of the stress and measurement techniques.

The survey methods of the inner diameter profiles and viscosity consist of several steps illustrated hereunder.

Step 1—Generation and Measurement of the Pressure Transients.

The transients are produced and recorded making use of the equipment illustrated in FIG. 16.

The different characteristic times of the phenomenon and of the method are illustrated in FIG. 2, which shows the trend of the pressure at the well head during a closing operation; the graph shows the different times in question.

The head pressure data must be acquired before the well closing operation (t=0) and during a time $t=t_{max}$. The time $t_{max}$ must be higher than the time $\Delta t_R$ required by the flow rate and pressure wave for reaching the end of the pipe tract in question and returning to the surface. The relationship between the length L of the pipe, the velocity c of the wave propagation and the back time $\Delta t_R$ is:

$$\Delta t_R = 2L/c$$

and can be used to determine any of the values, once the other two are known.

$\delta t$ will indicate the time span between the PM values measured of:

$$PM(t) \, t=0, \delta t, 2\delta t, \ldots t_{max}.$$

The PM values measured in this phase are the starting data necessary for processing the subsequent phases.

Step 2—Interpolation of the Flow Rate Transient.

In this phase, the PM data measured during the fast closing operation (first item of phase 1), are interpolated: starting from a flow rate value of zero Q(t=0)=0, the curve of Q(t) is obtained which best allows the head pressure change due to the transient to be interpolated.

The third and last phase varies in relation to the variable which is to be obtained. Immediately after the closing of the duct, it is normally useful to determine the real profile of the inner diameters of the duct. In this case we have:

Step 3—Calculation of the Diameter Profile Along the Duct.

In this step, by using the values measured in step 1 and the law of the flow rate variation obtained in step 2, a profile of the diameters of the pipe D(ξ) is obtained, such as to reproduce the evolution of the pressure measured in the time span $\Delta t_R$.

In practice, starting from the element $E_k$, where k is given by $$k=\xi/\lambda$$

the value of the diameter is adjusted so as to adapt the simulated head pressure with the real pressure, with a constant increase in time:

$D_{k+j}^{down}$ is modified so that $$P_{simulated}(\Delta t_p+jdt)=P_{measured}(\Delta t_p+jdt) j=1,2,\ldots$$

until all the diameters have been adapted. In this way, in a single passage, all the values of the diameters along the production pipeline starting from the experimental pressure values, are obtained.

The same logic can be subsequently used for determining the viscosity profile:

Step 3'—Calculation of the Viscosity Profile Along the Duct.

In this step, the profile of the fluid viscosity values along the pipe η(ξ) is obtained, so as to reproduce the evolution of the pressure measured in the time span $\Delta t_R$, by using the values measured in step 1 and the law of the flow rate variation obtained in step 2.

In practice, starting from the element $E_k$, where k is given by:

$$k=\xi/\lambda$$

the diameter value is adjusted so as to adapt the simulated head pressure with the real pressure, at an ever-increasing time:

η(k+j) is modified so that $$P_{simulated}(\Delta t_p+jdt)=P_{measured}(\Delta t_p+jdt) \text{ for } j=1,2,\ldots$$

until all the diameters have been adapted. In this way, in a single passage, all values of viscosity along the production pipeline starting from the experimental values of pressure, are obtained.

It is easy to adapt the same procedure to the determination of other variables associated with the duct or to the fluid, which can be of interest for a certain application.

Pipeline Having a Constant Inner Real Diameter

A simplified procedure is described hereunder which can be used for determining the viscosity of the fluid present in the duct when the duct has a uniform real inner diameter.

In this case, the stress produced by means of the equipment of FIG. 16 has the behaviour illustrated in FIG. 21. The pressure peaks, starting from the first rebound, progressively decrease in intensity until they can no longer be recorded by means of the measuring apparatus. The drop in the peak amplitude depends, among other things, on the viscosity of the fluid present in the duct.

FIG. 25 shows the logarithm, for numerous liquid viscosity values, of the amplitude of peaks represented in FIG. 21, normalised with respect to the amplitude of the first rebound.

The amplitude of each peak is calculated, for the construction of the figure, as the difference, in absolute value, between the base, evaluated before the peak itself, and its more extreme point. The curves represent different viscosities and show that, from the first rebound onwards, the $\log_{10}$ of the peak drop in the subsequent rebounds, follows an approximately linear law. The slope of the straight line which interpolates, once the fluid viscosity in the duct has been established, the $\log_{10}$ of the amplitude of the pressure peaks in relation to the rebound numbers on the pipe ends (from the first onwards), will be called hereunder "fading coefficient" and expressed as α. FIG. 25 therefore suggests that the fading coefficient is a function of the viscosity, and this is indicated in FIG. 26.

From a more careful theoretical investigation, it can be observed that the fading coefficient is proportional to the pressure drops which will take place in the duct, under stationary conditions, if the fluid flow rate is constant and equal to the maximum of the flow rate peak generated by the equipment of FIG. 16.

In the example illustrated herein, the fading coefficient of the peaks normalised with respect to the first rebound, is proportional to the pressure drops at the stationary flow rate of 15 m³/h (maximum peak value of FIG. 17). In the example considered, when the viscosity is higher than 0.9 mPas, the flow is laminar, whereas for lower viscosities, the flow is turbulent. The transition from lamellar to turbulent flow is the origin of the "step" present in FIG. 26.

Experience shows that, in the presence of dispersion phenomena which lead to the progressive widening of the pressure peaks in the subsequent rebounds, the amplitude of each peak must be substituted with the area of its first half. In the formula, with reference to FIG. 27, it is necessary to substitute the area $A_j$ of each peak at its height $H_j$.

With reference to the object of the present invention, if the viscosity of the fluid present in the pipeline, due to a structuring process, progressively increases along the pipe, the generation of flow rate transients by means of the apparatus of FIG. 16 and the measurement of the corresponding coefficient of the pressure peak drop, will provide a rapid quantitative indication of the viscosity evolution of the fluid and consequently a simple control method of the entire process. If the fluid viscosity is considerably non-homogeneous along the duct, for example due to strong temperature variations, or the inner diameter is not constant, then the viscosity estimation should be effected by means of the other analysis methods specified above.

What is claimed is:

1. A process for reducing a restart pressure of streams selected from waxy crude oils, water-in-crude emulsions and dispersions of hydrocarbon hydrates, at least partially structured, in which a mechanical disturbance is applied on said streams, having:

temperatures lower than a WAT (Wax Appearance Temperature) for waxy crudes and water-in-crude emulsions;

temperatures lower than forming temperatures of said hydrates and pressures higher than forming pressure of said hydrates, for dispersions of hydrocarbon hydrates, wherein the mechanical disturbance is affected by a shear stress, flow rate and pressure waves, mixing with a liquid having a different density with respect to the streams, insufflation of inert gas, sound or infrasound waves and is applied under flow-stop conditions and before said streams reach a maximum structuring degree.

2. The process according to claim 1, wherein the sound or infrasound waves are obtained by pressure and flow rate waves.

3. The process according to claim 1, wherein the insufflation of inert gas is effected at a pressure higher than 1 bar.

4. The process according to claim 1, wherein the temperature of the waxy crudes is lower than a Pour Point (PP) temperature.

5. The process according to claim 1, wherein water is present in the emulsions in a quantity of up to 70% by weight.

6. The process according to claim 1, wherein the mechanical disturbance must have an intensity, expressed as shear stress or stress generated by the pressure wave, which is higher than 15% of a yield stress of the stream at the moment in which said stress begins.

7. The process according to claim 6, wherein the intensity is higher than 20% and lower than 40% of the yield stress of the stream, at the moment said stress begins.

* * * * *